US007198946B2

(12) United States Patent
Marton et al.

(10) Patent No.: US 7,198,946 B2
(45) Date of Patent: Apr. 3, 2007

(54) SCREENING FOR AGENTS EFFECTIVE IN DECREASING ABNORMAL MACROPHAGES ASSOCIATED WITH AMYOTROPHIC LATERAL SCLEROSIS

(75) Inventors: Laurence J. Marton, Palo Alto, CA (US); Tennore M. Ramesh, Westwood, MA (US); Sean Scott, San Francisco, CA (US); Michael McGrath, Burlingame, CA (US)

(73) Assignee: Pathologica, LLC, San Francisco, CA (US)

( * ) Notice: Subject to any disclaimer, the term of this patent is extended or adjusted under 35 U.S.C. 154(b) by 289 days.

(21) Appl. No.: 10/299,946

(22) Filed: Nov. 18, 2002

(65) Prior Publication Data

US 2003/0175832 A1 Sep. 18, 2003

Related U.S. Application Data

(60) Provisional application No. 60/333,263, filed on Nov. 16, 2001.

(51) Int. Cl.
*C12N 5/08* (2006.01)
*G01N 33/53* (2006.01)
*C12Q 1/02* (2006.01)
(52) U.S. Cl. .................. 435/368; 435/7.24; 435/29
(58) Field of Classification Search .............. 435/7.24, 435/325; 514/2
See application file for complete search history.

(56) References Cited

U.S. PATENT DOCUMENTS

| 4,935,449 A | 6/1990 | Bey et al. .................... 514/671 |
| 5,498,522 A | 3/1996 | Porter ........................... 435/6 |
| 6,638,506 B1 | 10/2003 | Schubert | |
| 7,105,183 B2 | 9/2006 | McGrath | |

FOREIGN PATENT DOCUMENTS

| WO | WO 99/21542 | 5/1999 |
| WO | WO 99/29731 | 6/1999 |
| WO | WO 00/74718 | 12/2000 |

OTHER PUBLICATIONS

Zhang et al. Evidence for systemic immune system alterations in sporadic amyotrophic lateral sclerosis (ALS). Journal of Neuroimmunology. 2005;159:215-224.*
Bensimon, G. et al., "A Controlled Trial of Riluzole in Amyotrophic Lateral Sclerosis" (1994) New Eng. J. Med. 330:858-591.
Deng, H. et al., "Amyotrophic Lateral Sclerosis and Structural Defects in Cu,Zn Superoxide Dismutase" (1993) Science 261:1047-1051.
Ferrante. R. et al., "Increased 3-Nitrotyrosine and Oxidative Damage in Mice with a Human Copper/Zinc Superoxide Dismutase Mutation" (1997) Ann. Neurol. 42(3):326-334.

Ferrante, R. et al., "Evidence of Increased Oxidative Damage in Both Sporadic and Familial Amyotrophic Lateral Sclerosis" (1997) J. Neurochem. 69:2064-2074.
Gredal, O. et al., "Muscarinic, N-Methyl-D-Aspartate (NMDA) and Benzodiazepine Receptor Binding Sites in Cortical Membranes from Amyotrophic Lateral Sclerosis Patients" (1996) J. Neurol. Sci. 143:121-125.
Gurney, M. et al., "Motor Neuron Degeneration in Mice that Express a Human Cu,Zn Superoxide Dismutase Mutation" (1994) Science 264:1772-1775.
Hall, E. et al., "Relationship of Oxygen Radical-Induced Lipid Perioxidative Damage to Disease Onset and Progression in a Transgenic Model of Familial ALS" (1998) J. Neurosci. Res. 53:66-77.
International Search Report mailed on Aug. 29, 2003, for PCT patent application No. PCT/US02/37178, filed Nov. 18, 2002, 8 pages.
Kalra, S. et al., "Biological Markers in the Diagnosis and Treatment of ALS" (1999) J. Neurol. Sci. 165:S27-S32.
Kramer, D. et al., "Use of 4-Fluoro-L-Ornithine to Monitor Metabolic Flux Through the Polyamine Biosynthetic Pathway" (1995) Biochem. Pharmacol. 50:1433.
Lacomblez, L. et al., "Dose-Ranging Study of Riluzole in Amyotrphic Lateral Sclerosis" (1996) Lancet 347:1425-1431.
Marton, L. and Pegg, A., "Polyamines As Targets for Therapeutic Intervention" (1995) Ann. Rev. Pharm. Toxicol. 35:55-91.
McGeer, P. et al., "Reactions of the Immune System in Chronic Degenerative Neurological Diseases" (1991) Can. J. Neurol. Sci. 18:376-379.
McGeer et al., (1989) Clinical and Investigative Medicine 12(suppl. 4):B43.
Mukhopadhyaya, R. et al., "Effects of Bis(benzyl)polyamine Analogs on Leishmania donovani Promastigotes" (1995) Exp. Parasit. 81:39-46.
Olivera, A. et al., "Expression of HLA-DR in Pheripheral Nerve of Amyotrophic Lateral Sclerosis" (1994) Arq. Neuropsiquiatr. 52:493-500.
O'Sullivan, M. et al., "Polyamine Derivatives as Inhibitors of Trypanothione Reductase and Assessment of their Trypanocidal Activities" (1997) Bioorg. Med. Chem. 5:2145-2155.

(Continued)

*Primary Examiner*—Phillip Gambel
*Assistant Examiner*—Chun Crowder
(74) *Attorney, Agent, or Firm*—Cooley Godward Kronish LLP

(57) ABSTRACT

The invention provides methods of monitoring amyotrophic lateral sclerosis (ALS) disease development or progression and monitoring an ALS therapy by determining the level of HLA-DR expression by CD14+ monocytes and/or the percentage of CD16+ cells in the population of CD14+ cells and/or the number of CD14+/CD16+ cells in peripheral blood of an individual with ALS. The invention is also directed to methods for decreasing the number of circulating CD14+ monocytes and/or the population of CD14+/CD16+ cells and/or the number of CD14+/CD16+ cells in an individual with ALS. The invention is also directed to methods of screening for agents which decrease the population of CD14+ monocytes with elevated HLA-DR expression and/or the population of CD14+/CD16+ cells and/or the number of CD14+/CD16+ cells in an individual with ALS.

3 Claims, 5 Drawing Sheets

OTHER PUBLICATIONS

Rosen, D et al., "Mutations in Cu/Zn Superoxide Dismutase Gene Are Associated with Familial Amyotrophic Lateral Slerosis" (1993) Nature 362:59-62.

Rothstein, J. et al., "Abnormal Excitatory Amino Acid Metabolism in Amyotrophic Lateral Sclerosis" (1990) Ann. Neurol. 28:18-25.

Rowland, L. et al., "Amyotrophic Lateral Sclerosis" (2001) N. Eng. J. Med. 344:1688-1700.

Schubert and Schwan, (1995) Neuroscience Letters 198:29-32.

Shaw, P. et al., CSF and Plasma Amino Acid Levels in Motor Neuron Disease: Elevation of CSF Glutamate in a Subset of Patients (1995) Neurodegeneration 4:209-216.

Troost, D. et al., "Immunohistological Alterations in Muscle of Patients with Amyotrophic Lateral Sclerosis: Mononuclear Cell Phenotypes and Expression of MHC Products" (1992) Clin. Neuropathol. 11:115-120.

Virgo, L. et al., "Induction of the Immediate Early Gene c-jun in Human Spinal Cord in Amyotrophic Lateral Sclerosis with Concomitant Loss of NMDA Receptor NR-1 and Glycine Transporter mRNA" (1995) Brain Res. 676:196-204.

Monk, P.N. and P.J. Shaw, "ALS: life and death in a bad neighborhood," Nature Medicine, vol. 12, No. 8, pp. 885-887 (2006).

* cited by examiner

SCREENING FOR AGENTS EFFECTIVE IN DECREASING ABNORMAL MACROPHAGES ASSOCIATED WITH AMYOTROPHIC LATERAL SCLEROSIS

CROSS-REFERENCE TO RELATED APPLICATIONS

This application claims the priority benefit of U.S. Provisional application 60/333,263, filed Nov. 16, 2001, which is hereby incorporated by reference in its entirety.

TECHNICAL FIELD

The invention relates to the field of Amyotrophic Lateral Sclerosis (ALS) disease and immune function. More specifically, it pertains to the activated monocytes or abnormal macrophages and monitoring of ALS progression, monitoring ALS therapy and treating patients with ALS.

BACKGROUND ART

Amyotrophic lateral sclerosis (ALS), known colloquially as Lou Gehrig's disease, is a heterogeneous group of progressive neurodegenerative disorders characterized by a selective loss of upper and/or lower motor neurons in the brain and spinal cord. Affected individuals demonstrate a variety of symptoms including twitching and cramping of muscles, loss of motor control in hands and arms, impaired use of the arms and legs, weakness and fatigue, tripping and falling, dropping things, slurred or thick speech and difficulty breathing or swallowing. ALS eventually results in death of the affected individual.

Generally, ALS is neuropathologically characterized by degeneration of motor neurons in the brainstem, spinal cord and cerebral cortex. Clinically, ALS is typically characterized by progressive muscle weakness, wasting and fasiculations (i.e., cramping), in conjunction with spasticity, hyperreflexia and pathological corticospinal tract findings.

Excitotoxicity and oxidative stress appear to be at least two pathogenic mechanisms that participate in motor neuron cell death in ALS (Kalra et al. (1999) *J. Neurol. Sci.* 165:S27–S32). Among the support for a role for excitotoxicity in ALS is the findings of elevated glutamate levels in cerebrospinal fluid of patients with ALS and changes in the number or function of glutamate receptors in the central nervous system (CNS) of patients with ALS (Rothstein et al. (1990) *Ann. Neurol.* 28:18–25; Shaw et al. (1995) *Neurodegeneration* 4:209–216; Gredal et al. (1996) *J. Neurol. Sci.* 143:121–125; Virgo et al. (1995) *Brain Res.* 676:196–204). Much support for the role of oxidative stress and reactive oxygen species in ALS has come from the discovery of mutations in the gene for superoxide dismutase (SOD1) in some familial cases of ALS (Deng et al. (1993) *Science* 261:1047–1051; Rosen et al. (1993) *Nature* 362:59–62). Motor neurons in transgenic mice expressing human mutant SOD1 have been shown to be selectively vulnerable to free radical damage (Gurney et al. (1994) *Science* 264:1772–1775) and oxidative changes in proteins, lipids and nucleic acids have been identified in CNS tissue from patients with ALS and in the SOD1 transgenic mice. (Ferrante et al. (1997) *J. Neurochem.* 69:2064–2074; Hall et al. (1998) *J. Neurosci. Res.* 53:66–77; Ferrante et al. (1997) *Ann. Neurol.* 42:326–334).

Immune dysfunction has also been proposed to be linked to ALS. For example, evidence of a cell mediated immune response was identified in ALS spinal cord. For example, helper and cytotoxic T lymphocytes and reactive microglia expressing the major histocompatibility glycoproteins HLA-A, B, C and HLA-DR were found in ALS spinal cord (McGeer et al. (1991) *Can. J. Neurol. Sci.* 18:376–379). Cellular infiltrates consisting mainly of T lymphocytes and macrophages were found in muscle biopsy specimens from autopsied ALS patients (Troost et al. (1992) *Clin. Neuropathol.* 11:115–120). Most of the T lymphocytes and macrophages surrounding the atrophied muscle fibers expressed a high level of HLA-DR indicating an activated state of the cells and suggesting a role for the cells in ALS-associated muscle atrophy. Also, Schwann cells expressing HLA-DR have been identified in the endoneurium of peripheral nerve in ALS (Olivera et al. (1994) *Arq. Neuropsiquiatr.* 52:493–500).

ALS is diagnosed using a variety of tests and examinations, including muscle and nerve biopsy, spinal tap, X-rays, magnetic resonance imaging (MRI) and electrodiagnostic tests, many of which involve invasive procedures or complex imaging and analysis. There remains a need for an easily accessible measure of ALS disease progression for use in monitoring of the disease as well as in evaluation of potential therapies for ALS.

All publications and patent applications cited herein are hereby incorporated by reference in their entirety.

DISCLOSURE OF THE INVENTION

The present invention provides methods of monitoring therapy of ALS in an individual comprising detecting the level of HLA-DR expression by CD14+ cells and/or level of abnormal macrophages in a sample of peripheral blood from the individual.

Accordingly, in one aspect of the invention, the effect of an ALS therapy is determined by comparing the level of HLA-DR expression by CD14+ cells and/or the number of CD14+/CD16+ cells and/or the percentage of CD16+ cells in a population of CD14+ cells in peripheral blood before and during treatment, with a downward trend in HLA-DR expression and/or in the number of CD14+/CD16+ cells and/or the percentage of CD16+ cells in a population of CD14+ cells generally being consistent with a positive effect.

The present invention also provides methods of monitoring development or progression of ALS in a patient with ALS comprising determining the level of abnormal macrophages in a peripheral blood sample from the ALS patient.

Accordingly, in another aspect of the invention, monitoring of ALS is done by comparing the level of HLA-DR expression by CD14+ cells and/or the number of CD14+/CD16+ cells and/or the percentage of CD16+ cells in a population of CD14+ cells in peripheral blood at different time points in the course of the disease, with a increase in HLA-DR expression and/or an increase in the number of CD14+/CD16+ cells and/or the percentage of CD16+ cells in a population of CD14+ cells generally being consistent with an increase in disease severity and/or rate of progression.

The invention also provides methods for decreasing the number of CD14+ monocytes, preferably activated circulating monocytes, in an ALS individual by administering to the individual an amount of a polyamine analog effective to decrease the number of CD14+ monocytes in the individual.

In another aspect, the invention provides methods for decreasing the number of activated circulating monocytes in an ALS individual by administering to the individual an amount of a polyamine analog effective to decrease the number of activated circulating monocytes in the individual.

The invention also provides methods for decreasing the number of abnormal macrophages in an individual with ALS disease by administering to the individual an amount of a polyamine analog effective to decrease the number of CD14+ cells with elevated HLA-DR expression in the individual.

The invention also provides methods for decreasing the number of abnormal macrophages in an individual with ALS disease by administering to the individual an amount of a polyamine analog effective to decrease the number of CD14+/CD16+ cells in the individual.

The invention also provides methods of screening for agents effective for decreasing the number of CD14+ monocytes, preferably activated circulating monocytes, associated with ALS.

The invention also provides methods for screening for an agent effective in decreasing the number of abnormal macrophages associated with ALS through determining the difference in viability of CD14+ cells with elevated HLA-DR expression in the presence and in the absence of a candidate agent, where the CD14+ cells with elevated HLA-DR expression are obtained from a blood sample from an individual with ALS.

The invention also provides methods for screening for an agent effective in decreasing the number of abnormal macrophages associated with ALS through determining the difference in viability of CD14+/CD16+ cells in the presence and in the absence of a candidate agent, where the CD14+/CD16+ cells are obtained from a blood sample from an individual with ALS.

The invention also provides methods for aiding diagnosis or prediction of ALS through detection of elevated HLA-DR expression by CD14+ cells and/or an increase in the number of CD14+/CD16+ cells and/or the percentage of CD16+ cells in a population of CD14+ cells from a blood sample from an individual. In some embodiments, detection of such abnormal macrophages is combined with one or more other disease indicators for diagnosis of ALS.

The invention also provides methods for aiding diagnosis of ALS disease through detecting abnormal macrophages in a blood sample of an individual, where the detecting includes detection of CD14+ cells with elevated HLA-DR expression. The invention also provides methods for aiding diagnosis of ALS disease through detecting abnormal macrophages in a blood sample of an individual, where the detecting includes detection of CD14+/CD16+ cells.

In some embodiments of the invention, the blood sample is analyzed for the presence of abnormal macrophages within about 12 hours after the blood sample is collected.

MODES FOR CARRYING OUT THE INVENTION

Figure 1:
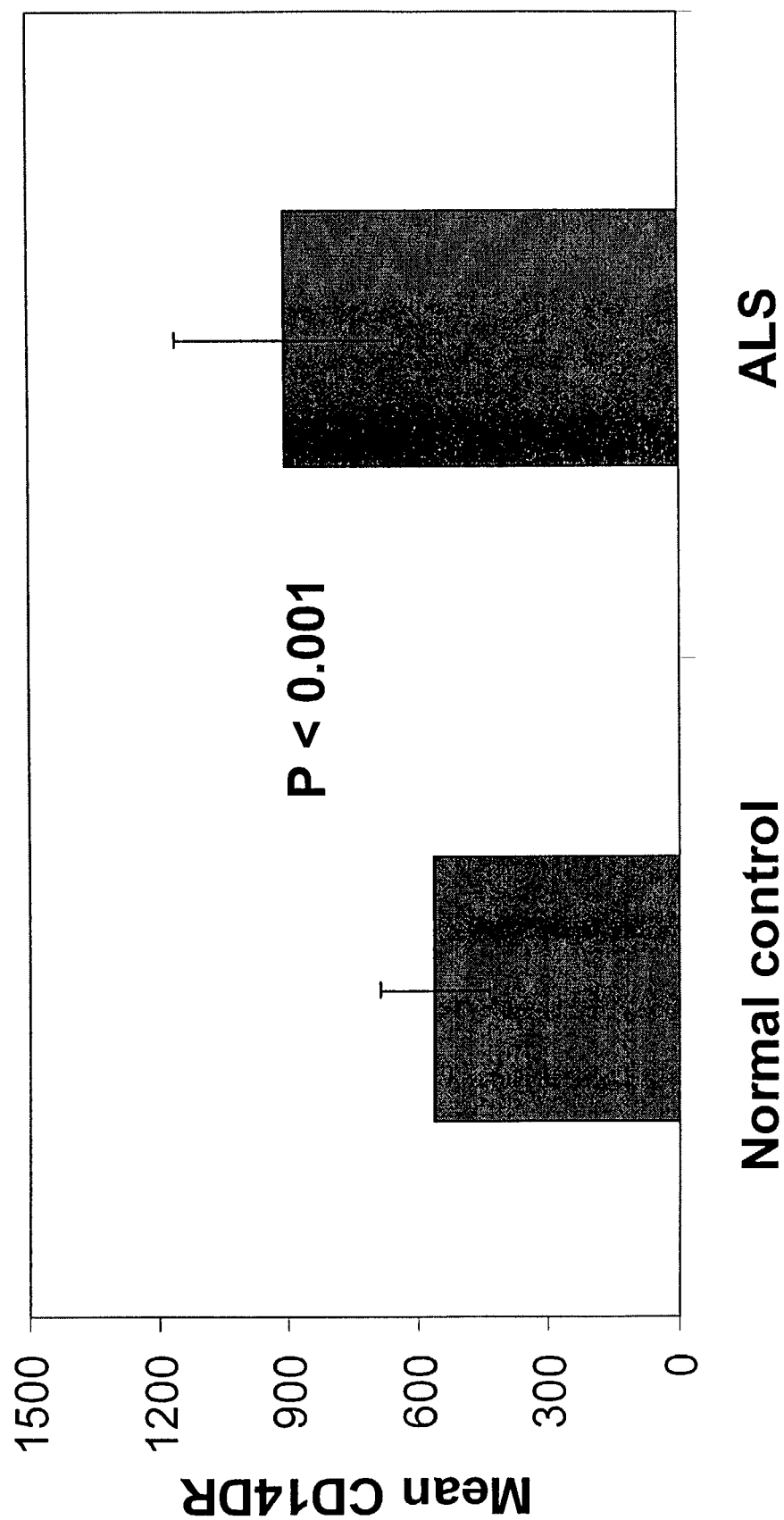
FIG. 1 is a bar graph depicting the level of HLA-DR expression on CD14+ monocytes from peripheral blood samples of ALS patients (ALS) and non-ALS individuals (normal control).

We have discovered that circulating monocytes (from peripheral blood) in patients with ALS are generally abnormally activated and/or differentiated (generally and interchangeably referred to herein as "activated circulating monocytes" and "abnormal macrophages") as compared to monocytes from peripheral blood samples from non-ALS individuals. We have also observed evidence of proliferation of these cells. Thus, we have discovered methods for monitoring ALS disease progression and/or activity as well as methods for monitoring effectiveness of agents for the treatment of ALS. Our discovery also indicates a potentially significant target for therapeutic intervention, as these abnormal cells may mediate at least one symptom of the disease.

These activated monocytes or abnormal macrophages in the peripheral blood from ALS patients are generally indicated by CD14 expression and overall elevated levels of HLA-DR and/or by CD14 and CD16 expression, generally without identifiable concomitant T cell activation in the ALS individuals.

We have also observed that treatment of peripheral blood mononuclear cells from ALS patients with anti-proliferative agents, such as polyamine analogs, results in a decrease in the number of activated CD14+ monocytes (or abnormal macrophages) in peripheral blood cells from patients with ALS.

Accordingly, the invention provides methods for monitoring ALS disease progression, including before, during and/or after a treatment regimen, or in the absence of treatment, by determining the level of abnormal macrophages in a biological sample, preferably a blood sample, from an ALS patient. The invention also provides methods for monitoring the effectiveness of an ALS therapy agent(s) and/or protocol by determining the level of abnormal macrophages in a biological sample, preferably a blood sample, from an ALS patient before, during and/or after administration of the therapy. The invention also provides methods for decreasing the number of activated CD14+ monocytes in a patient with ALS, which alone or in conjunction with other treatment modalities may delay development of and/or ameliorate one or more symptoms of ALS. As discussed below, preferred agents for decreasing the number of activated CD14+ monocytes in an ALS patient are polyamine analogs.

Definitions

As used herein, the terms "macrophage" and "monocyte" are used interchangeably, as it is understood that in the art the term "monocyte" is often used to describe a circulating mononuclear cell that expresses the CD14 cell surface marker, and when in a tissue this cell is also classified as a macrophage.

An "abnormal macrophage" or "activated circulating monocyte" or "activated monocyte" as used interchangeably herein denotes a monocyte which expresses CD14 (i.e., CD14+) and which expresses an elevated level of HLA-DR, the major histocompatibility antigen class II, and/or which expresses CD16 (i.e., CD16+). Generally, abnormal macrophages are found in peripheral blood but they may also be found in other biological samples from an individual. Generally, these abnormal macrophages are present without identifiable concomitant T cell activation in the ALS patients.

As used herein, detecting the "presence of abnormal macrophages" generally means detecting the level of abnormal macrophages. Generally, the level of abnormal macrophages (or activated monocytes) is indicated by the level of HLA-DR expression in a population of CD14+ cells and/or the percentage of CD16+ cells in a population of CD14+ cells and/or the number of CD14+/CD16+ cells, although other markers that indicate monocyte activation, differentiation and/or proliferation could be used. It is understood that an absolute or even relative level need not be determined; an observation of detectable abnormal macrophages is sufficient.

"Amyotrophic lateral sclerosis" or "ALS" are terms understood in the art and as used herein to denote a progressive neurodegenerative disease that affects upper motor neurons (motor neurons in the brain) and/or lower motor neurons (motor neurons in the spinal cord) and results in motor neuron death. As used herein, the term "ALS" includes all of the classifications of ALS known in the art, including, but not limited to classical ALS (typically affecting both lower and upper motor neurons), Primary Lateral Sclerosis (PLS, typically affecting only the upper motor neurons), Progressive Bulbar Palsy (PBP or Bulbar Onset, a version of ALS that typically begins with difficulties swallowing, chewing and speaking), Progressive Muscular Atrophy (PMA, typically affecting only the lower motor neurons) and familial ALS (a genetic version of ALS).

A "proliferating macrophage" is a term understood in the art and as used herein denotes a macrophage which is dividing. Normally a macrophage is a terminally differentiated cell incapable of further division. For purposes of this invention, a "proliferating macrophage" is capable of further division or is in a portion of the cell cycle not considered to be terminal or end stage. Methods of detecting proliferating macrophage(s) are discussed below.

As used herein, detecting the "presence of proliferating macrophages" generally means detecting the level of proliferating macrophages. It is understood that an absolute or even relative level need not be determined; an observation of detectable proliferating macrophages is sufficient.

An "individual" is a vertebrate, preferably a mammal, more preferably a human. Mammals include, but are not limited to, farm animals, sport animals, rodents, primates, and pets. An "ALS individual" or an "ALS patient" is an individual who is diagnosed as having ALS or is suspected of having ALS by demonstrating ALS-associated symptoms.

A "non-ALS individual" is an individual who is not diagnosed as having ALS or not suspected of having ALS. ALS and methods of diagnosing ALS are known in the art and are discussed herein.

As used herein, "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples. Generally, the sample will be, or be derived from, peripheral blood and as such is a "blood sample". In some cases, the blood will have been enriched for a macrophage fraction, by using, for example, glass or plastic adherence.

A "blood sample" is a biological sample which is derived from blood, preferably peripheral (or circulating) blood. A blood sample may be, for example, whole blood, plasma or serum.

As used herein, methods for "aiding diagnosis" means that these methods assist in making a clinical determination regarding the classification, or nature, of the ALS, and may or may not be conclusive with respect to the definitive diagnosis. Accordingly, a method of aiding diagnosis of ALS can comprise the step of detecting the level of abnormal macrophages in a biological sample from the individual and/or determining the level of HLA-DR expression by CD14+ cells in a biological sample from the individual, preferably a peripheral blood sample. In various embodiments, the level of abnormal macrophages can be detected by determining the percentage of CD16+ cells in a population of CD14+ cells and/or the number of CD14+/CD16+ cells in the biological sample, preferably a peripheral blood sample.

"Development" or "progression" of ALS herein means initial manifestations and/or ensuing progression of the disorder. Development of ALS can be detectable and assessed using standard clinical techniques, such as nerve and muscle biopsy and CNS scanning technologies such as MRI. However, development also refers to disease progression that may be undetectable. For purposes of this invention, development or progression refers to the biological course of the disease state. "Development" includes occurrence, recurrence, and onset. As used herein "onset" or "occurrence" of ALS includes initial onset and/or recurrence.

As used herein, "delaying development" of ALS means to defer, hinder, slow, retard, stabilize, and/or postpone development of the disease. This delay can be of varying lengths of time, depending on the history of the disorder and/or the medical profile of the individual being treated. As is evident to one skilled in the art, a sufficient or significant delay can, in effect, encompass prevention, in that the individual does not develop detectable disease. A method that "delays" development of disease is a method that reduces the extent of the disease in a given time frame, when compared to not using the method. Such comparisons are typically based on clinical studies, using a statistically significant number of subjects, although this knowledge can be based upon anecdotal evidence. "Delaying development" can mean that the extent and/or undesirable clinical manifestations are lessened and/or time course of the progression is slowed or lengthened, as compared to not administering the agent. Thus the term also includes, but is not limited to, alleviation of symptoms, diminishment of extent of disease, stabilized (i.e., not worsening) state of disease, delay or slowing of disease progression, and remission (whether partial or total) whether detectable or undetectable.

As used herein, an "effective amount" (e.g., of an agent) is an amount (of the agent) that produces a desired and/or beneficial result. An effective amount can be administered in one or more administrations. In some embodiments, an effective amount is an amount sufficient to decrease the level of abnormal macrophages in an ALS patient or derived from an ALS individual. An "amount sufficient to decrease the level of abnormal macrophages" preferably is able to decrease the level of abnormal macrophages by at least about 25%, preferably at least about 50%, more preferably at least about 75%, and even more preferably at least about 90%. Such a decrease may have desirable concomitant effects, such as to palliate, ameliorate, stabilize, reverse, slow or delay progression of disease, delay and/or even prevent onset of disease.

In other embodiments, "amount sufficient to decrease the level of HLA-DR expression by CD14+ cells" preferably is able to decrease the level of HLA-DR expression by at least about 25%, preferably at least about 50%, more preferably at least about 75%, and even more preferably at least about 90%. Such a decrease may have desirable concomitant effects, such as to palliate, ameliorate, stabilize, reverse, slow or delay progression of disease, delay and/or even prevent onset of disease.

As used herein, decreasing the "level of abnormal macrophages" generally means decreasing the population number of abnormal macrophages or activated monocytes and/or decreasing the level of HLA-DR expression in a population of CD14+ cells. In various embodiments, the level of abnormal macrophages can be assayed by determining the percentage of CD16+ cells in a population of CD14+ cells and/or the number of CD14+/CD16+ cells in the biological sample. It is understood that an absolute level need not be determined; an observation of a relative level of abnormal macrophages is sufficient.

As used herein, the term "agent" means a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic compounds based on various core structures, and these are also included in the term "agent". In addition, various natural sources can provide compounds, such as plant or animal extracts, and the like. Agents include, but are not limited to, polyamine analogs. Agents can be administered alone or in various combinations.

"Modulating" macrophage proliferation means that the rate of proliferation is altered when compared to not administering an agent that changes macrophage proliferation. For example, "modulating" macrophage proliferation through use of a polyamine analog means that the rate of proliferation is altered when compared to not administering an agent that interferes with natural polyamine interaction with DNA (including, but not limited to, interfering with a polyamine biosynthetic pathway, interfering with the intracellular concentration of spermidine, competitors, inhibitors of DNA interaction by a natural polyamine, interfering with polyamine metabolism, etc.), such as a polyamine analog.

Preferably, "modulating" macrophage proliferation means a change in the rate of macrophage proliferation of at least 25%, preferably at least 50%, more preferably at least 75%, and even more preferably at least 90%. Generally, for purposes of this invention, "modulating" macrophage proliferation means that the rate of proliferation is decreased when compared to the rate of proliferation in that individual when no agent is administered. However, during the course of therapy, for example, it may be desirable to increase the rate of proliferation from a previously measured level. The degree of modulation may be assessed by measurement of macrophage proliferation, which will be discussed below, and generally entails detecting a proliferation marker(s) in a macrophage population or uptake of certain substances such as BrdU or 3H-thymidine (which would provide a quantitative measure of proliferation). Further, it is possible that, if the macrophages are proliferating due to a genetic alteration (such as transposition, deletion, or insertion), this alteration could be detected using standard techniques in the art, such as RFLP (restriction fragment length polymorphism).

A "target" of a polyamine or polyamine analog is an entity which interacts, either directly or indirectly, with the polyamine or polyamine analog(s). Examples of targets are DNA, RNA, and/or membranes.

The term "alkyl" refers to saturated aliphatic groups including straight-chain, branched-chain, cyclic groups, and combinations thereof, having the number of carbon atoms specified, or if no number is specified, having up to 12 carbon atoms. "Straight-chain alkyl" or "linear alkyl" groups refers to alkyl groups that are neither cyclic nor branched, commonly designated as "n-alkyl" groups. Examples of alkyl groups include, but are not limited to, groups such as methyl, ethyl, n-propyl, isopropyl, butyl, n-butyl, isobutyl, sec-butyl, t-butyl, pentyl, n-pentyl, hexyl, heptyl, octyl, nonyl, decyl, undecyl, dodecyl, neopentyl, cyclopropyl, cyclobutyl, cyclopentyl, cyclohexyl, and adamantyl. Cyclic groups can consist of one ring, including, but not limited to, groups such as cycloheptyl, or multiple fused rings, including, but not limited to, groups such as adamantyl or norbornyl. Preferred subsets of alkyl groups include $C_1$–$C_{12}$, $C_1$–$C_{10}$, $C_1$–$C_8$, $C_1$–$C_6$, $C_1$–$C_4$, $C_1$–$C_2$, $C_3$–$C_4$, $C_3$, and $C_4$ alkyl groups.

"Substituted alkyl" refers to alkyl groups substituted with one or more substituents including, but not limited to, groups such as halogen (fluoro, chloro, bromo, and iodo), alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of substituted alkyl groups include, but are not limited to, —$CF_3$, —$CF_2$—$CF_3$, and other perfluoro and perhalo groups.

"Hydroxyalkyl" specifically refers to alkyl groups having the number of carbon atoms specified substituted with one —OH group. Thus, "$C_3$ linear hydroxyalkyl" refers to —$CH_2CH_2CHOH$—, —$CH_2CHOHCH_2$—, and —$CHOHCH_2CH_2$—.

The term "alkenyl" refers to unsaturated aliphatic groups including straight-chain (linear), branched-chain, cyclic groups, and combinations thereof, having the number of carbon atoms specified, or if no number is specified, having up to 12 carbon atoms, which contain at least one double bond (—C=C—). Examples of alkenyl groups include, but are not limited to, —$CH_2$—CH=CH—$CH_3$; and —$CH_2$—$CH_2$-cyclohexenyl, where the ethyl group can be attached to the cyclohexenyl moiety at any available carbon valence.

The term "alkynyl" refers to unsaturated aliphatic groups including straight-chain (linear), branched-chain, cyclic groups, and combinations thereof, having the number of carbon atoms specified, or if no number is specified, having up to 12 carbon atoms, which contain at least one triple bond (—C≡C—). "Hydrocarbon chain" or "hydrocarbyl" refers to any combination of straight-chain, branched-chain, or cyclic alkyl, alkenyl, or alkynyl groups, and any combination thereof. "Substituted alkenyl," "substituted alkynyl," and "substituted hydrocarbon chain" or "substituted hydrocarbyl" refer to the respective group substituted with one or more substituents, including, but not limited to, groups such as halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

"Aryl" or "Ar" refers to an aromatic carbocyclic group having a single ring (including, but not limited to, groups such as phenyl) or multiple condensed rings (including, but not limited to, groups such as naphthyl or anthryl), and includes both unsubstituted and substituted aryl groups. "Substituted aryls" refers to aryls substituted with one or more substituents, including, but not limited to, groups such as alkyl, alkenyl, alkynyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group.

"Heteroalkyl," "heteroalkenyl," and "heteroalkynyl" refer to alkyl, alkenyl, and alkynyl groups, respectively, that contain the number of carbon atoms specified (or if no number is specified, having up to 12 carbon atoms) which contain one or more heteroatoms as part of the main, branched, or cyclic chains in the group. Heteroatoms include, but are not limited to, N, S, O, and P; N and O are preferred. Heteroalkyl, heteroalkenyl, and heteroalkynyl groups may be attached to the remainder of the molecule either at a heteroatom (if a valence is available) or at a carbon atom. Examples of heteroalkyl groups include, but are not limited to, groups such as —O—$CH_3$, —$CH_2$—O—$CH_3$, —$CH_2$—$CH_2$—O—$CH_3$, —S—$CH_2$—$CH_2$—$CH_3$, —$CH_2$—NH($CH_3$)—S—$CH_3$, —$CH_2$—$CH_2$—NH—$CH_2$—$CH_2$—, 1-ethyl-6-propylpiperidino, 2-ethylthiophenyl, and morpholino. Examples of heteroalkenyl groups include, but are not limited to, groups such as —CH=CH—NH—CH($CH_3$)—$CH_2$—. "Heteroaryl" or "HetAr" refers to an aromatic carbocyclic group having a single ring (including, but not limited to, examples such as pyridyl, thiophene, or furyl) or multiple condensed rings (including, but not limited to, examples such as imidazolyl, indolizinyl or benzothienyl) and having at least one hetero atom, including, but not limited to, heteroatoms such as N, O, P, or S, within the ring. Unless otherwise specified, heteroalkyl, heteroalkenyl, heteroalkynyl, and heteroaryl groups have between one and five heteroatoms and between one and twelve carbon atoms. "Substituted heteroalkyl," "substituted heteroalkenyl," "substituted heteroalkynyl," and "substituted heteroaryl" groups refer to heteroalkyl, heteroalkenyl, heteroalkynyl, and heteroaryl groups substituted with one or more, including, but not limited to, groups such as alkyl, alkenyl, alkynyl, benzyl, hydrocarbon chains, halogen, alkoxy, acyloxy, amino, hydroxyl, mercapto, carboxy, benzyloxy, phenyl, benzyl, cyano, nitro, thioalkoxy, carboxaldehyde, carboalkoxy and carboxamide, or a functionality that can be suitably blocked, if necessary for purposes of the invention, with a protecting group. Examples of such substituted heteroalkyl groups include, but are not limited to, piperazine, substituted at a nitrogen or carbon by a phenyl or benzyl group, and attached to the remainder of the molecule by any available valence on a carbon or nitrogen, —NH—$SO_2$-phenyl, —NH—(C=O)O-alkyl, —NH—(C=O)O-alkyl-aryl, and —NH—(C=O)-alkyl. If chemically possible, the heteroatom(s) as well as the carbon atoms of the group can be substituted. The heteroatom(s) can also be in oxidized form, if chemically possible.

The term "alkylaryl" refers to an alkyl group having the number of carbon atoms designated, appended to one, two, or three aryl groups.

The term "alkoxy" as used herein refers to an alkyl, alkenyl, alkynyl, or hydrocarbon chain linked to an oxygen atom and having the number of carbon atoms specified, or if no number is specified, having up to 12 carbon atoms. Examples of alkoxy groups include, but are not limited to, groups such as methoxy, ethoxy, and t-butoxy.

The term "alkanoate" as used herein refers to an ionized carboxylic acid group, such as acetate (CH3C(=O)—O(-1)), propionate (CH3CH2C(=O)—O(-1)), and the like. "Alkyl alkanoate" refers to a carboxylic acid esterified with an alkoxy group, such as ethyl acetate (CH3C(=O)—O—CH2CH3). "ω-haloalkyl alkanoate" refers to an alkyl alkanoate bearing a halogen atom on the alkanoate carbon atom furthest from the carboxyl group; thus, ethyl ω-bromo propionate refers to ethyl 3-bromopropionate, methyl ω-chloro n-butanoate refers to methyl 4-chloro n-butanoate, etc.

The terms "halo" and "halogen" as used herein refer to Cl, Br, F or I substituents.

For all of the foregoing definitions, preferred subsets of the groups include $C_1$–$C_{12}$, $C_1$–$C_{10}$, $C_1$–$C_8$, $C_1$–$C_6$, $C_1$–$C_4$, $C_1$–$C_2$ (when chemically possible), $C_3$–$C_4$, $C_3$, and $C_4$ groups.

"Protecting group" refers to a chemical group that exhibits the following characteristics: 1) reacts selectively with the desired functionality in good yield to give a protected substrate that is stable to the projected reactions for which protection is desired; 2) is selectively removable from the protected substrate to yield the desired functionality; and 3) is removable in good yield by reagents compatible with the other functional group(s) present or generated in such projected reactions. Examples of suitable protecting groups can be found in Greene et al. (1991) *Protective Groups in Organic Synthesis*, 3rd Ed. (John Wiley & Sons, Inc., New York). Amino protecting groups include, but are not limited to, mesitylenesulfonyl (Mts), benzyloxycarbonyl (CBz or Z), t-butyloxycarbonyl (Boc), t-butyldimethylsilyl (TBS or TBDMS), 9-fluorenylmethyloxycarbonyl (Fmoc), tosyl, benzenesulfonyl, 2-pyridyl sulfonyl, or suitable photolabile protecting groups such as 6-nitroveratryloxy carbonyl (Nvoc), nitropiperonyl, pyrenylmethoxycarbonyl, nitrobenzyl, dimethyl dimethoxybenzil, 5-bromo-7-nitroindolinyl, and the like. Hydroxyl protecting groups include, but are not limited to, Fmoc, TBS, photolabile protecting groups (such as nitroveratryl oxymethyl ether (Nvom)), Mom (methoxy methyl ether), and Mem (methoxy ethoxy methyl ether), NPEOC (4-nitrophenethyloxycarbonyl) and NPEOM (4-nitrophenethyloxymethyloxycarbonyl).

"Polyamine analog" is defined as an organic cation structurally similar but non-identical to polyamines such as spermine and/or spermidine and their precursor, diamine putrescine. "Polyamine" is defined as any of a group of aliphatic, straight-chain amines derived biosynthetically from amino acids; several polyamines are reviewed in Marton et al. (1995) *Ann. Rev. Pharm. Toxicol.* 35:55–91. Polyamines cadaverine and putrescine are diamines produced by decarboxylation of lysine or ornithine, respectively. Putrescine is converted to spermidine, and spermidine to spermine, by the addition of an aminopropyl group. This group is provided by decarboxylated S-adenosyl methionine.

By "conformationally restricted" is meant that, in a polyamine analog, at least two amino groups are locked or limited in spatial configuration relative to each other. The relative movement of two amino groups can be restricted, for example, by incorporation of a cyclic or unsaturated moiety between adjacent nitrogens (exemplified, but not limited to, a ring, such as a three-carbon ring, four-carbon ring, five-carbon-ring, six-carbon ring, or a double or triple bond, such as a double or triple carbon bond), where the adjacent nitrogens are not included in the conformationally-restricted group. Groups restricting conformational flexibility by means of steric hindrance, yet structurally favorable to the anti-proliferative effects, can also be used for conformational restriction. A "conformationally restricted" polyamine analog can comprise at least two amino groups which are conformationally restricted relative to each other, but can also further comprise amino groups which are not conformationally restricted relative to each other. Flexible molecules such as spermine and BE-444 can have a myriad of conformations and are therefore not conformationally restricted. In both polyamines and polyamine analogs, whether conformationally restricted or not, the amino groups are aliphatic and not aromatic.

As used herein, "a", "an", and "the" can mean singular or plural (i.e., can mean one or more) unless indicated otherwise.

Methods of the Invention

The present invention provides methods of monitoring therapy of ALS in an individual comprising detecting the level of HLA-DR expression by CD14+ cells and/or the level of abnormal macrophages and/or the percentage of CD16+ cells in a population of CD14+ cells and/or the number of CD14+/CD16+ cells in a sample of peripheral blood from the individual. The present invention also provides methods of monitoring development or progression of ALS in a patient with ALS comprising determining the level of abnormal macrophages and/or the level of HLA-DR expression by CD14+ cells and/or the percentage of CD16+ cells in a population of CD14+ cells and/or the number of CD14+/CD16+ cells in a peripheral blood sample from the ALS patient. The invention also provides methods for decreasing the number of CD14+ monocytes, preferably activated circulating monocytes, in an ALS patient. The invention also provides methods of screening for agents effective for decreasing the number of CD14+ monocytes, preferably activated circulating monocytes in an ALS patient.

As elevated HLA-DR expression on CD14+ cells and/or increased numbers of CD14+/CD16+ cells and/or the percentage of CD16+ cells in a population of CD14+ cells is associated with ALS, monitoring these levels may in turn indicate initial responsiveness and/or efficacy, as well as the appropriate dosage of the therapy. It is understood that monitoring therapy means that biological sample(s) are obtained at different times, for example, during application of therapy, and are compared, either with each other, a control, and/or a desired value. In one embodiment, monitoring therapy includes the step of determining the level of HLA-DR expression by CD14+ cells from peripheral blood. In another embodiment, monitoring therapy includes the step of determining the level of CD14+ cells expressing elevated HLA-DR in a blood sample, preferably peripheral blood. In another embodiment, monitoring therapy includes the step of determining the percentage of CD16+ cells in the population of CD14+ cells in a blood sample, preferably peripheral blood. In another embodiment, monitoring therapy includes the step of determining the number of CD14+/CD16+ cells in a blood sample, preferably peripheral blood. In another embodiment, the level of abnormal macrophages (in various embodiments, the level of CD14+ cells expressing elevated HLA-DR; the percentage of CD16+ cells in the population of CD14+ cells and/or the number of CD14+/CD16+ cells) in a blood sample determined during and/or at completion of the therapy is generally compared with the level in a control sample and/or with a desired value. In another embodiment, monitoring therapy also includes the step of measuring proliferation of the abnormal macrophages.

For the purpose of monitoring an ALS therapy in one embodiment, the level of abnormal macrophages in a sample taken at a particular time from a patient undergoing the therapy and/or a sample taken after or at completion of the therapy is generally compared with the level in a sample taken from the patient prior to the therapy and/or with the level in a sample taken from the patient at a different time point in the therapy. For example, a decrease in the level of abnormal macrophages in the sample taken during therapy as compared to the sample taken prior to or at an earlier time point in therapy would generally be consistent with a positive effect of the ALS therapy.

In one embodiment, for the purpose of monitoring an ALS therapy, the level of abnormal macrophages is assessed by the determining the level of HLA-DR expression by CD14+ cells from a blood sample, such as a peripheral blood sample. For example, the effect of a therapy is determined by comparing the level of HLA-DR expression by CD14+ cells in peripheral blood before and during treatment, with a downward trend in HLA-DR expression generally being consistent with a positive effect.

In one embodiment, for the purpose of monitoring an ALS therapy, the level of abnormal macrophages is assessed by the determining the percentage of CD16+ cells in the population of CD14+ cells from a blood sample, such as a peripheral blood sample. For example, the effect of a therapy is determined by comparing the percentage of CD16+ cells in the population of CD14+ cells in peripheral blood before and during treatment, with a downward trend in the percentage of CD14+/CD16+ cells generally being consistent with a positive effect.

In one embodiment, for the purpose of monitoring an ALS therapy, the level of abnormal macrophages is assessed by the determining the number of CD14+/CD16+ cells in a blood sample, such as a peripheral blood sample. For example, the effect of a therapy is determined by comparing the number of CD14+/CD16+ cells in peripheral blood before and during treatment, with a downward trend in the number of CD14+/CD16+ cells generally being consistent with a positive effect.

In those individuals with ALS, determination of the level of HLA-DR expression by CD14+ cells and/or the percentage of CD16+ cells in the population of CD14+ cells and/or the number of CD14+/CD16+ cells in a biological sample, e.g., peripheral blood, may also assist in monitoring development or progression of the disease. Thus, the invention also includes methods of monitoring disease development or progression in an individual with ALS, comprising determining the level of HLA-DR expression by CD14+ cells and/or the percentage of CD16+ cells in the population of CD14+ cells and/or the number of CD14+/CD16+ cells and/or the level of abnormal macrophages in a peripheral blood sample from that individual. Preferably, the individual is "afflicted with" (e.g., diagnosed as having, suffering from and/or displaying one or more clinical symptoms of) ALS.

As the level of HLA-DR expression by CD14+ cells and/or the percentage of CD16+ cells in the population of CD14+ cells and/or the number of CD14+/CD16+ cells is associated with ALS, monitoring these levels may provide an indication of changes in the development or progression of the disease. It is understood that monitoring an individual with ALS generally means that biological sample(s) are obtained at different times, for example, over weeks, months and/or years, and are compared with each other, a control, and/or a desired value. In another embodiment, monitoring disease development or progression in an individual with ALS also includes the step of measuring proliferation of the abnormal macrophages. In monitoring of ALS, an increase in HLA-DR expression by CD14+ cells and/or an increase in the percentage of CD16+/CD14+ cells and/or an increase in the number of CD14+/CD16+ cells is generally consistent with an increase in disease severity and/or rate of progression.

In those individuals considered at high or significant risk of developing ALS, determining the level of HLA-DR expression by CD14+ cells and/or the percentage of CD16+/CD14+ cells and/or the number of CD14+/CD16+ cells in a biological sample may also assist in alerting the individual and/or the clinician of possible precursor disease. Thus, the invention also includes methods of monitoring an individual at risk or high risk of developing ALS, comprising determining the level of HLA-DR expression by CD14+ cells and/or determining the number of CD14+/CD16+ cells and/or the percentage of CD16+ cells in the population of CD14+ cells in a biological sample from that individual. Preferably, the individual is displaying one or more clinical symptoms associated with ALS, or at "risk" for (e.g., having a genetic predisposition for, or family history of, or being environmentally exposed to factors which increase the probability of acquiring) ALS. In monitoring an individual at risk or high risk of developing ALS, an elevated level of HLA-DR expression by CD14+ cells and/or an increase in the percentage of CD14+/CD16+ cells in blood and/or an increase in the number of CD14+/CD16+ cells is generally consistent with an increase in risk of development of a symptom of ALS disease.

It is understood that monitoring an individual at (high) risk generally, but not necessarily, means that biological sample(s) are obtained at different times, for example, over weeks, months and/or years, and are compared with each other, a control, and/or a desired value. In one embodiment, monitoring an individual at (high) risk includes the step of determining the level of HLA-DR expression by CD14+ cells and/or the percentage of CD16+ cells in the population of CD14+ cells in a sample and/or the number of CD14+/CD16+ cells of peripheral blood. In another embodiment, monitoring an individual at (high) risk also includes the step of measuring proliferation of the abnormal macrophages.

For the purpose of monitoring a therapy, monitoring disease development or progression, or monitoring an individual at (high) risk, generally the level of HLA-DR expression by CD14+ cells and/or the percentage of CD16+/CD14+ cells and/or the number of CD14+/CD16+ cells in a sample may be compared with the mean or median level in samples taken from healthy individuals or from non-ALS patients, matched where necessary for sex and/or age. Alternatively, results of these indicia can be compared with the values or the mean or median values of results from samples taken from the same monitored individual at various time points. A difference or change in the level of HLA-DR expression by CD14+ cells and/or the number of CD14+/CD16+ cells and/or the percentage of CD16+ cells in the population of CD14+ cells from the ALS samples when compared to that of the non-ALS samples generally correlates with a change in the disease development or activity. For example, an increase in HLA-DR expression by CD14+ cells and/or in the percentage of CD16+ cells in a population of CD14+ cells and/or the number of CD14+/CD16+ cells correlates with an increase in ALS progression.

In combination with one or more other disease indicators, the detection of elevated HLA-DR expression by CD14+ cells and/or an increase in the number of CD14+/CD16+ cells and/or an increase in the percentage of CD16+ cells in a population of CD14+ cells may aid in diagnosis or prediction of ALS. The differential diagnosis will include any condition associated with ALS as a causative or consequential effect, with the ultimate diagnosis being the responsibility of the managing physician or clinician. Accordingly, the invention includes methods of aiding diagnosis of ALS. These methods generally comprise the step of determining the level of HLA-DR expression by CD14+ cells and/or in the percentage of CD16+ cells in a population of CD14+ cells and/or the number of CD14+/CD16+ cells and/or the level of abnormal macrophages in a blood sample from the individual suspected of having ALS.

To determine an elevated level of HLA-DR expression, the mean or median level of HLA-DR expression is determined on a population of CD14+ cells from an ALS individual. Levels of HLA-DR expression can be calculated as the number of HLA-DR molecules per cell obtained from a blood sample (or detected in a biological sample). More usually, the level is calculated as a mean per cell of HLA-DR detecting signal (e.g., fluorescence intensity) for the CD14+ population of cells in the sample. The level may be compared to an HLA-DR level from the same individual measured at a different time and/or under different conditions (such as before treatment, different dose, etc.).

In some embodiments, HLA-DR level is compared to a mean or median level of HLA-DR expression determined on a population of CD14+ cells from a non-ALS standard, for example from a non-ALS individual or non-ALS individuals. A finding of HLA-DR expression level of greater than about 1.4 fold that of the non-ALS standard is indicative of an elevated level of HLA-DR expression in the ALS individual. Generally, a finding of HLA-DR expression level of greater than about 1.5 fold, greater than about 1.6 fold, greater than about 1.7 fold, greater than about 1.8 fold, greater than about 1.9 fold, greater than about 2.0 fold, greater than about 5.0 fold, or greater than about 10 fold that of a non-ALS standard is indicative of an elevated level of HLA-DR expression in the ALS individual.

The level of expression of HLA-DR, major histocompatibility antigen class II, by CD14+ monocytes can be determined using methods known in the art, such as general flow cytometry technology, as described in Current Protocols of Immunology (J. E. Coligan et al., eds., 1999). Methods known in the art, including general flow cytometry, can also be used to determine CD16 expression on cells, including on CD14+ cells. Generally, cells from a blood sample of an individual can be stained for one or more cellular antigens using one or more antibodies specific for the antigens including anti-CD14 antibodies, anti-CD16 antibodies and anti-HLA-DR antibodies. When cells are assayed for expression of more than one antigen, the cells may be stained with the antigen-specific antibodies simultaneously or sequentially. Alternatively, cells expressing a particular antigen can be separated from the non-expressing cells and then the isolated population of cells can be stained for expression of any other antigen. The antigen-specific antibodies can be directly labeled with a fluorophore or indirectly labeled using fluorophore conjugated anti-antibody antibodies (i.e., secondary antibodies). After reacting with the antigen-specific antibodies and being fluorescently labeled, the cells are analyzed using a flow cytometer, such as the Becton Dickinson FACScan. The level of HLA-DR expression on CD14+ cells can be quantified based on data collected from the flow cytometer. See, for example, Example 1. Co-expression of CD14 and CD16 on a cell can also be determined based on flow cytometric data.

The level of HLA-DR expression in CD14+ monocytes can also be determined by other techniques known in the art. For example, CD14+ cells can be isolated from other blood cells and components using, for example, antibody-based electronic cell sorting techniques, as described for example in Current Protocols in Immunology (J. E. Coligan et al., eds., 1999). The level of HLA-DR expression by isolated CD14+ cells can be determined by analysis of mRNA and/or protein from the cells. The amount of HLA-DR RNA in the CD14+ cells can be measured by various techniques known in the art including, but not limited to, S1 nuclease analysis, ribonuclease protection assay, primer extension assay, RNA blot analysis (e.g., northern and/or slot blot hybridization) and quantitative RT-PCR, as described, for example, in Current Protocols in Molecular Biology (F. M. Ausubel et al., eds., 1987). The amount of HLA-DR protein in and/or on the surface of the CD14+ cells can be measured using various techniques known in the art including, but not limited to, quantitative immunoassays, such as, radioimmunoassay, immunofluorescent assay, enzyme immunoassay, chemiluminescent assay, ELISA, or Western blot assay, as described in Current Protocols in Immunology (J. E. Coligan et al., eds., 1999). Techniques such as these can also be used to measure expression of CD16 in or on CD14+ monocytes.

The biological samples to be analyzed are maintained in appropriate conditions prior to analysis so that abnormal macrophages, if present in the sample, are detectable at time of analysis. In some embodiments, cells of the biological sample to be analyzed are maintained with sufficient unchelated calcium including, but not limited to, in the container into which the biological sample is collected and in the medium in which the cells of the sample are stored until analysis. This is not meant to convey that no calcium chelator can be present and no calcium can be chelated. For instance, in some embodiments, any calcium chelator present with the cells of the biological sample to be analyzed is present in an amount less than what is sufficient to interfere with blood coagulation. Conversely, in some embodiments, maintaining cells to be analyzed in an amount of calcium chelator sufficient to interfere with blood coagulation is to be avoided. In some embodiments, cells of the biological sample to be analyzed are maintained with no calcium chelator present. As shown in Example 2, in the absence of the calcium chelator, the percentage of CD14+/CD16+ cells in the ALS samples was greater than 4 fold higher than the percentage of CD14+/CD16+ cells in the non-ALS samples. However, the presence of a calcium chelator in the biological sample resulted in a decrease of the number of detectable CD14+/CD16+ cells in the ALS samples to within the range of CD14+/CD16+ cells in non-ALS samples. Thus, in these peripheral blood samples, the presence of the calcium chelator interfered with the usefulness of the number of CD14+/CD16+ cells as an indicator of ALS.

In some embodiments, determination of CD14, CD16 and/or HLA-DR expression of the analyzed cells is performed on the same day that the biological sample is collected (i.e., "same day" analysis). In other embodiments, determination of CD14, CD16 and/or HLA-DR expression is performed on the day after the sample was collected (i.e., "second day" analysis). In some embodiments, determination of CD14, CD16 and/or HLA-DR expression of the analyzed cells is performed within about 96 hours, within about 72 hours, within about 60 hours, within about 48 hours, within about 36 hours, within about 24 hours, within about 18 hours, within about 12 hours, within about 6 hours of blood collection, within about 4 hours of blood collection or within about 2 hours of blood collection. In some embodiments, the biological sample analyzed is blood, preferably peripheral blood. In some embodiments, the peripheral blood sample is collected into containers containing heparin.

In some embodiments, the number of CD14+/CD16+ cells or the percentage of CD16+ cells in a population of CD14+ cells is compared to a mean or median level of CD14+/CD16+ cells in a biological sample from a non-ALS standard, for example from a non-ALS individual or non-ALS individuals. A finding of a percentage of CD16+ cells in a population of CD14+ cells and/or the number of CD14+/CD16+ cells in a sample of greater than about 1.5 fold, greater than about 1.6 fold, greater than about 1.7 fold, greater than about 1.8 fold, greater than about 1.9 fold, greater than about 2.0 fold, greater than about 3.0 fold, greater than about 4.0 fold, greater than about 5.0 fold, or greater than about 10 fold that of a non-ALS standard is indicative of an increased number of CD14+/CD16+ cells in the ALS individual.

Generally, these abnormal macrophages are detected in an individual with ALS or at risk of developing ALS without the detection of concomitant T cell activation or with reduced level of T cell activation relative to what one skilled in the art would expect to observe with elevated HLA-DR expression by CD14+ monocytes and/or increased numbers of CD14+/CD16+ cells and /or increased percentage of CD16+ cells in a population of CD14+ cells. T cell activation can be assessed using methods and standards known in the art. For example, the level of T cell activation can be determined by the expression of particular cell activation markers on the cells, including, but not limited to CD4, CD8 and/or CD38, and by the number of cells in the present in the population expressing such markers. As shown in Example 1, the T cell populations in peripheral blood from ALS individuals were comparable to those from normal (non-ALS) individuals as indicated by the CD4/CD38 and CD8/CD38 cell populations.

As described above, in some cases, the population of CD14+ cells expressing elevated HLA-DR includes proliferating macrophages. Also described above, in some cases, the population of CD14+/CD16+ cells includes proliferating macrophages. Measuring of proliferating macrophage(s) can be achieved using any of several techniques. In some embodiments of the invention, proliferation of abnormal macrophages is measured in relation to total circulating macrophages, and is performed on a leukocyte preparation from peripheral blood. In other embodiments of the invention, proliferation is measured in relation to tissue-fixed macrophages, typically performed on tissue sections. Proliferating macrophages may be detected, for example, by assaying cell proliferative markers, such as PCNA, Ki67 or uptake of bromodeoxyuridine (BrdU) or 3H-thymidine. These markers are distinct from those that identify only "activated" macrophages (as opposed to proliferating macrophages), such as CD69 and CD25. The cellular subset representing macrophages may in turn be identified by detection of certain cell specific markers, such as CD14, CD68, CD16, or nonspecific esterase. Detection of these cell-type and/or proliferative markers use methods standard in the art, such as staining techniques and FACS sorting and analysis. These methods are further described in Example 3. Further, it is possible that these proliferating macrophages could be distinguished based on other characteristics, such as cell density (as measured in PERCOLL™ gradients, for example). These determinations may be established empirically using standard techniques in the art.

The invention provides methods for screening for agents that decrease the level of abnormal macrophages in ALS patients. As an example, for the general screening of agents effective in decreasing the level of abnormal macrophages associated with ALS, peripheral blood cells are isolated from an individual affected with ALS. The level of and/or viability abnormal macrophages is determined in the sample, the sample of cells is treated with the candidate agent, and the effect is compared with cells not treated. For example, a decrease in the level and/or viability of abnormal macrophages in the treated sample as compared to the untreated sample would indicate that the candidate agent may be effective in decreasing the level and/or viability of abnormal macrophages in a patient with ALS. When administered to a patient, the effect of a candidate agent is determined by comparing the level of abnormal macrophages before and during treatment, with a downward trend of abnormal macrophages generally being consistent with a positive effect. In various embodiments, determining the level of abnormal macrophages includes the determination of the level of CD14+ monocytes with elevated HLA-DR expression and/or the number of CD14+/CD16+ cells and/or the percentage of CD16+ cells in a population of CD14+ cells in a biological sample. Generally, techniques and reagents for assessing cell viability, including CD14+ cell viability, are well-known in the art.

The invention provides methods for screening for agents that decrease the number of CD14+ monocytes, preferably activated CD14+ monocytes and/or CD14+ monocytes with elevated HLA-DR expression and/or the number of CD14+/CD16+ cells and/or the percentage of CD16+ cells in a population of CD14+ cells from ALS patients. Indicia of decreasing the number of such CD14+ cells from ALS patients, includes, but is not limited to, decreasing viability of the cells and/or decreasing the number of the cells in a biological sample. As an example, for the general screening of agents effective in decreasing the number of CD14+ monocytes associated with ALS, peripheral blood cells are isolated from an individual affected with ALS. The number of CD14+ monocytes is determined in the sample, the sample of cells is treated with the candidate agent, and the effect is compared with cells not treated. For example, a decrease in the level of number of CD14+ monocytes in the treated sample as compared to the untreated sample would indicate that the candidate agent may be effective in decreasing the level of number of CD14+ monocytes in a patient with ALS. When administered to a patient, the effect of a candidate agent is determined by comparing the level of number of CD14+ monocytes, preferably activated CD14+ monocytes, before and during treatment, with a downward trend of number of CD14+ monocytes generally being consistent with a positive effect.

The invention provides methods for decreasing the number of CD14+ monocytes, preferably activated CD14+ monocytes, in a patient with ALS comprising administering a polyamine analog, a salt of a polyamine analog, or a protected derivative of a polyamine analog, in an amount sufficient to decrease the level of number of CD14+ monocytes, preferably activated CD14+ monocytes and/or CD14+ monocytes with elevated HLA-DR expression and/or the number of CD14+/CD16+ cells and/or the percentage of CD16+ cells in a population of CD14+ cells in the individual (i.e., an effective amount). An "amount sufficient to decrease the number of CD14+ monocytes" preferably is able to decrease the number of CD14+ monocytes by at least about 25%, preferably at least about 50%, more preferably at least about 75%, and even more preferably at least about 90%. Such a decrease may have desirable concomitant effects, such as to palliate, ameliorate, stabilize, reverse, slow and/or delay progression of disease, delay or even prevent onset of disease.

In another embodiment, a composition comprising a polyamine analog, or a protected derivative of a polyamine analog is administered to an ALS patient in an amount sufficient to modulate macrophage proliferation (i.e., an effective amount). Polyamine analogs are discussed below and herein.

Various compounds herein disclosed can be used in the methods of the invention. The compounds can be used in their free base or free acid form (that is, as the free compound and not as a salt). Additionally, any pharmaceutically acceptable salt(s) of the compound(s) can also be used. Pharmaceutically acceptable salts are those salts which retain the biological activity of the free compounds and which are not biologically or otherwise undesirable. The desired salt of a basic compound may be prepared by methods known to those of skill in the art by treating the compound with an acid. Examples of inorganic acids include, but are not limited to, hydrochloric acid, hydrobromic acid, sulfuric acid, nitric acid, and phosphoric acid. Examples of organic acids include, but are not limited to, formic acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, sulfonic acids, and salicylic acid. Salts of basic compounds with amino acids, such as aspartate salts and glutamate salts, can also be prepared. The desired salt of an acidic compound can be prepared by methods known to those of skill in the art by treating the compound with a base. Examples of inorganic salts of acid compounds include, but are not limited to, alkali metal and alkaline earth salts, such as sodium salts, potassium salts, magnesium salts, and calcium salts; ammonium salts; and aluminum salts. Examples of organic salts of acid compounds include, but are not limited to, procaine, dibenzylamine, N-ethylpiperidine, N,N'-dibenzylethylenediamine, and triethylamine salts. Salts of acidic compounds with amino acids, such lysine salts, can also be prepared.

Stereoisomers of the compounds disclosed can also be used in the invention, including diastereomers and enantiomers, as well as mixtures of stereoisomers, including, but not limited to, racemic mixtures. Unless stereochemistry is explicitly indicated in a structure, the structure is intended to embrace all possible stereoisomers of the compound depicted.

For purposes of this invention, an individual suitable for administration of a polyamine analog is one who has been diagnosed as having ALS, or who is adjudged to be at high risk for developing such a disorder. An "at risk" or "high risk" individual is an individual who has a discrete and significant risk of developing ALS. An "at risk" or "high risk" individual may or may not have detectable disease, and may or may not have displayed detectable disease prior to receiving the method(s) described herein. "High risk" (or "at risk") denotes that an individual has one or more so-called risk factors, which are measurable parameters that correlate with development of disease. An individual having one or more of these risk factors has a higher probability of developing disease than an individual without these risk factor(s). These risk factors include, but are not limited to, genetic (i.e., hereditary) considerations (including family history and genetic markers). It is understood that having only one risk factor can often indicate high risk. The clinician, as one skilled in the art, has discretion to determine whether treatment using an agent may be indicated for an individual at risk.

In another embodiment, the invention provides methods for modulating macrophage proliferation in an individual with ALS comprising administering a composition comprising an effective amount of an agent that interferes with polyamine interaction with proliferating macrophage target, such as DNA, RNA, and/or membranes. An agent that interferes with polyamine interaction with a proliferating macrophage target(s) is one which interferes with any aspect of natural polyamine synthesis and/or metabolism, intracellular concentration regulation, and/or function (i.e., interaction with DNA).

Agents for Decreasing CD14+ Monocytes

In some embodiments of the invention, effecting a decrease in the level of preferably abnormal macrophages (i.e., CD14+ monocytes with elevated expression of HLA-DR and/or CD14+/CD16+ monocytes and/or the percentage of CD16+ cells in a population of CD14+ cells from ALS patients) is accomplished by using a polyamine analog (including stereoisomers, salts, and protected derivatives thereof). In other embodiments, any agent which decreases abnormal macrophage proliferation may be used. Such antiproliferative agents are known in the art. With respect to polyamine analogs, it is understood that the discussion also applies to stereoisomers, salts and protected derivatives thereof.

Polyamine Analogs

The polyamine analogs used in the present invention include compounds of the structures 1, 2, 3, 4, and 5, and the corresponding stereoisomers, salts, and protected derivatives thereof:

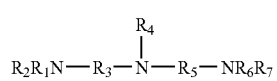

where $R_1$, $R_2$, $R_4$, $R_6$ and $R_7$ are independently selected from the group consisting of hydrogen, alkyl and aryl, and where $R_3$ and $R_5$ are alkyl groups;

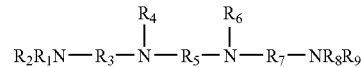

where $R_1$, $R_2$, $R_4$, $R_6$, $R_8$, and $R_9$ are independently selected from the group consisting of hydrogen, alkyl and aryl, and where $R_3$, $R_5$ and $R_7$ are alkyl groups;

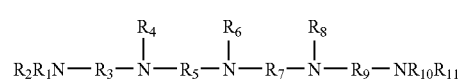

where $R_1$, $R_2$, $R_4$, $R_6$, $R_8$, $R_{10}$ and $R_{11}$ are independently selected from the group consisting of hydrogen, alkyl and aryl, and where $R_3$, $R_5$, $R_7$ and $R_9$ are alkyl groups;

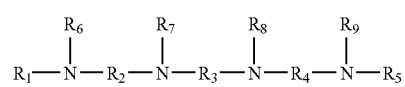

where $R_1$ and $R_5$ are independently selected from the group consisting of methyl, ethyl, n-propyl, and isopropyl;

where $R_2$, $R_3$, and $R_4$ are independently selected from the group consisting of $C_1$–$C_6$ alkyl, $C_2$–$C_6$ alkenyl, $C_3$–$C_6$ cycloalkyl, $C_1$–$C_6$ alkyl-$C_3$–$C_6$ cycloalkyl-$C_1$–$C_6$ alkyl, $C_3$–$C_{10}$ aryl, and $C_1$–$C_6$ alkyl-$C_3$–$C_{10}$ aryl-$C_1$–$C_6$ alkyl;

and where $R_6$, $R_7$, $R_8$ and $R_9$ are independently selected from the group consisting of H, methyl, and ethyl;

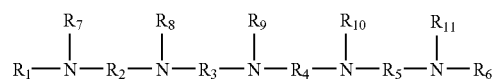

where $R_1$ and $R_6$ are independently selected from the group consisting of methyl, ethyl, n-propyl, and isopropyl;

where $R_2$, $R_3$, $R_4$ and $R_5$ are independently selected from the group consisting of $C_1$–$C_6$ alkyl, $C_2$–$C_6$ alkenyl, $C_3$–$C_6$ cycloalkyl, $C_1$–$C_6$ alkyl-$C_3$–$C_6$ cycloalkyl-$C_1$–$C_6$ alkyl, $C_3$–$C_{10}$ aryl, and $C_1$–$C_6$ alkyl-$C_3$–$C_{10}$ aryl-$C_1$–$C_6$ alkyl;

and where $R_7$, $R_8$, $R_9$, $R_{10}$ and $R_{11}$ are independently selected from the group consisting of H, methyl, and ethyl.

In some embodiments, the polyamine analogs will include compounds of the structure 3, where $R_3$, $R_5$, $R_7$ and $R_9$ are independently $(CH_2)_x$ groups, where x is an integer from 2 to 6, and further where $R_4$, $R_6$ and $R_8$ are hydrogen atoms.

In some embodiments, the polyamine analogs will include compounds of the structure 3, where R3, R5, R7 and R9 are independently $(CH2)_x$ groups, where x is an integer from 2 to 6, and where R4, R6 and R8 are hydrogen atoms, and where $R_1$ and $R_{10}$ are alkyl groups, and further where $R_2$ and $R_{11}$ are hydrogen atoms.

In some embodiments, the polyamine analogs will include compounds of the structure 3, where R3, R5, R7 and R9 are independently $(CH2)_x$ groups, where x is an integer from 2 to 6, and where R4, R6 and R8 are hydrogen atoms, and where $R_1$ and $R_{10}$ are alkyl groups, and where $R_2$ and $R_{11}$ are hydrogen atoms, and further where the polyamine analogs have a molecular weight less than 500.

In some embodiments, compounds also include compounds of the structure 4, where $R_6$, $R_7$, $R_8$ and $R_9$ are H;

where $R_1$ and $R_5$ are ethyl;

where $R_6$, $R_7$, $R_8$ and $R_9$ are H and $R_1$ and $R_5$ are ethyl;

and/or where $R_2$ and $R_4$ are independently selected from the group consisting of $C_1$–$C_6$ alkyl and $R_3$ is independently selected from the group consisting of $C_1$–$C_6$ alkyl, $C_2$–$C_6$ alkenyl, $C_3$–$C_6$ cycloalkyl, $C_1$–$C_6$ alkyl-$C_3$–$C_6$ cycloalkyl-$C_1$–$C_6$ alkyl, $C_3$–$C_{10}$ aryl, and $C_1$–$C_6$ alkyl-$C_3$–$C_{10}$ aryl-$C_1$–$C_6$ alkyl.

Additional polyamine analogs useful in the present invention include compounds of the formula 6, and the corresponding stereoisomers, salts, and protected derivatives thereof:

6

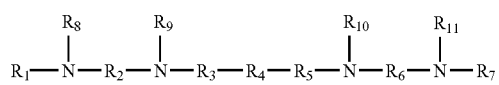

where $R_4$ is $C_2$–$C_6$ n-alkenyl, $C_3$–$C_6$ cycloalkyl, $C_3$–$C_6$ cycloalkenyl, or $C_3$–$C_6$ aryl;

$R_3$ and $R_5$ are independently chosen from a single bond, $C_1$–$C_6$ alkyl, or $C_1$–$C_6$ alkenyl;

$R_2$ and $R_6$ are independently chosen from $C_1$–$C_6$ alkyl, $C_1$–$C_6$ alkenyl, $C_3$–$C_6$ cycloalkyl, $C_3$–$C_6$ cycloalkenyl, or $C_3$–$C_6$ aryl;

$R_1$ and $R_7$ are independently chosen from H, $C_1$–$C_6$ alkyl, or $C_2$–$C_6$ alkenyl; and $R_8$, $R_9$, $R_{10}$, and $R_{11}$ are H.

In some embodiments of the compounds of formula 6, $R_1$ and $R_7$ are independently chosen from $C_1$–$C_6$ alkyl or $C_2$–$C_6$ alkenyl.

Additional polyamine analogs useful in the present invention include compounds of the formula 7, and the corresponding stereoisomers, salts, and protected derivatives thereof:

7

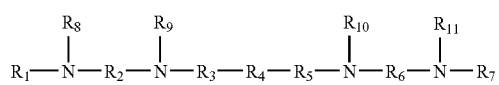

where $R_4$ is $C_1$–$C_6$ n-alkyl or $C_1$–$C_6$ branched alkyl;

$R_3$ and $R_5$ are independently chosen from a single bond or $C_1$–$C_6$ alkyl;

$R_2$ and $R_6$ are independently chosen from $C_1$–$C_6$ alkyl, $C_1$–$C_6$ alkenyl, $C_3$–$C_6$ cycloalkyl, $C_3$–$C_6$ cycloalkenyl, or $C_3$–$C_6$ aryl;

$R_1$ and $R_7$ are independently chosen from H, $C_1$–$C_6$ alkyl, or $C_2$–$C_6$ alkenyl; and $R_8$, $R_9$, $R_{10}$, and $R_{11}$ are H.

In some embodiments, the compounds of formula 7, R1 and R7 are independently chosen from C1–C6 alkyl or C2–C6 alkenyl, R4 is C1–C6 saturated n-alkyl or C1–C6 saturated branched alkyl, and R3 and R5 are independently chosen from a single bond or C1–C6 saturated n-alkyl.

In some embodiments, all the nitrogens of the polyamine analog are independently secondary, tertiary, or quarternary amino groups.

In some embodiments, polyamine analogs for use in this invention can be conformationally restricted.

Cyclic polyamine compounds and cyclic polyamine analogs are disclosed in International Patent Application WO 02/10142. In certain of these cyclic polyamine compounds, one or more of the aliphatic nitrogens form part of an amide group.

Among polyamine analogs for use in this invention are those compounds with a demonstrated ability to modulate naturally occurring polyamine levels in cells. Without intending to be limited by theory, possible mechanisms include competition in the polyamine synthesis pathway; upregulation of polyamine catabolizers such as SSAT; affecting polyamine metabolism.

Of special interest are the following polyamine analogs:

1,11-bis(ethyl)norspermine (1,11 -bis(ethylamino)-4,8-diazaundecane; BE-3-3-3)

1,8-bis(ethyl)spermidine (BES)

1,12-bis(ethyl)spermine (BESm; DESPM ($N^1$, $N^{12}$-diethylspermine; SunPharm);

1,14-bis(ethylamino)-5,10-diazatetradecane (BE-4-4-4) (Diethylhomospermine, $N^1$, $N^{14}$-diethylhomospermine; DEHOP or DEHSPM; SunPharm)

diethyl-norspermine (DENOP; SunPharm)

1,19-bis(ethylamino)-5,10,15-triazanonadecane (BE-4-4-4-4)

N-ethyl-N'-(2-(3'-ethylamino-propylamino methyl)-cis-cyclopropylmethyl)-propane 1,3-diamine tetrahydrochloride (SL-11037), provided by S'LIL, Madison, Wis.

N-ethyl-N'-(2-(3'-ethylamino-propylamino methyl)-trans-cyclobutylmethyl)-propane 1,3-diamine tetrahydrochloride (SL-11038), S'LIL N-ethyl-N'-(2-(3'-ethylamino-propylamino methyl)-trans-cyclopropylmethyl)-propane 1, 3-diamine tetrahydrochloride (SL-11044), S'LIL N,N'-bis(3-ethylaminopropyl)-cis-but-2-ene-1,4-diamine tetrahydrochloride (SL-11047, S'LIL) and its corresponding trans isomer (see WO 95/18091)

(5,10,15,20,25,30,35,40-Octaazatetratetracont-22-ene-1,44-diamine, N,N'-diethyl-, decahydrochloride, (22E)-) (SL-11144), S'LIL, which is assigned Chemical Abstracts Registry No. 304911-07-7

(5,10,15,20,25,30,35,40-Octaazatetratetracont-22-ene-1,44-diamine, N,N'-diethyl-, decahydrochloride, (22Z)-) (SL-11150), S'LIL, which is assigned Chemical Abstracts Registry No. 304911-08-8.

The structures of SL-11037, SL-11038, SL-11044, SL-11047, SL-11144 and SL-11150 are diagrammed below:

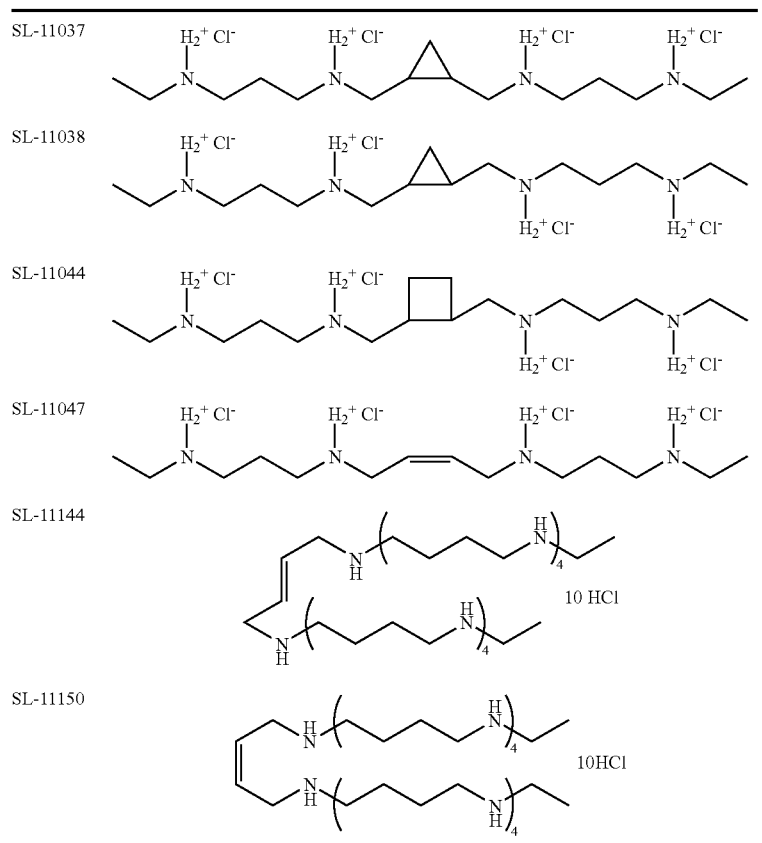

In addition, polyamine analogs as described in U.S. Patent Nos. 5,889,061, 5,880,161 and 5,541,230 and in international patent applications WO 00/66587, WO 00/66175, and WO 02/10142 may be used in the present invention.

Polyamine analogs, which can be branched or un-branched, include, but are not limited to, BE-4444 [1,19-bis(ethylamino)-5,10,15-triazanonadecane]; BE-333 [N1,N11-diethylnorspermine; DENSPM; 1,11-bis(ethylamino)-4,8-diazaundecane; thermine; Warner-Parke-Davis]; BE-33 [N1,N7-bis (ethyl) norspermidine]; BE-34 [N1,N8-bis (ethyl) spermidine]; BE-44 [N1,N9-bis (ethyl) homospermidine]; BE-343 [N1,N12-bis (ethyl) spermine; diethylspermine-N1-N12; DESPM]; BE-373 [N,N'-bis(3-ethylamino)propyl)-1,7-heptane diamine, Merrell-Dow]; BE-444 [N1,N14-bis (ethyl) homospermine; diethylhomospermine-N1-N14]; BE-3443 [1,17-bis (ethylamino)-4,9,14-triazaheptadecane]; BE-4334 [1,1 7-bis (ethylamino)-5,9,13-triazaheptadecane]; 1,12-Me$_2$-SPM [1,12-dimethylspermine]; various polyamine analogs disclosed in WO 98/17624 and U.S. Pat. No. 5,889,061; and the various novel polyamine analogs disclosed in WO 00/66175 and WO 00/66587, including, but not limited to, compounds designated SL-11027, SL-11028, SL-11029, SL-11033, SL-11034, SL-11037, SL-11038, SL-11043, SL-11044, SL-11047, SL-11048, SL-11050, SL-11090, SL-11091, SL-11092, SL-11093, SL-11094, SL-11098, SL-11099, SL-11100, SL-11101, SL-11102, SL-11103, SL-11104, SL-11105, SL-11108, SL-11114, SL-11118, SL-11119, SL-11121, SL-11122, SL-11123, SL-11124, SL-11126, SL-11127, SL-11128, SL-11129, SL-11130, SL-11132, SL-11133, SL-11134, SL-11136, SL-11137, SL-11141, SL-11144, SL-11150, SL-11201, and SL-11202. Additional polyamine analogs are known in the art, such as O'Sullivan et al. (1997) Bioorg. Med. Chem. 5:2145–2155; and Mukhopadhyaya et al. (1995) Exp. Parasit. 81:39–46; and U.S. Patent No. 4,935,449.

Besides the polyamine analogs listed above, stereoisomers, salts or protected derivatives thereof, may be used. The invention also comprises methods of using an effective amount of any of the polyamine analogs listed above, or stereoisomers, salts or protected derivatives thereof (or a composition comprising an effective amount of any of the polyamine analogs listed above, or stereoisomers, salts or protected derivatives thereof) in effecting a decrease in the number of abnormal macrophages or in decreasing macrophage proliferation associated with ALS (or in treating or delaying development of ALS). The invention also comprises any polyamine analog listed above, or stereoisomers, salts or protected derivatives thereof, for use in preparing compositions (i.e., medicaments) useful for treating ALS.

Any polyamine analog listed above, or stereoisomers, salts or protected derivatives thereof (or a composition comprising an effective amount of any polyamine analog listed above, or stereoisomers, salts or protected derivatives thereof) may be used in vitro or in vivo. In vitro, a suitable biological sample (such as a blood sample, which may or may not be enriched for the abnormal macrophage population) is contacted with the composition(s). In vivo, a composition of the invention is generally administered according to the manufacturer's/supplier's instructions. Generally, polyamine analogs are administered by subcutaneous or intravenous injection. They may also be administered orally.

The amount of a polyamine analog (or stereoisomers, salts or protected derivatives thereof) administered will depend on several variables, such as the particular analog (or stereoisomer, salt or protective derivative) used, the time course of administration, the condition of the individual, the desired objective, the extent of disease, how many doses will be administered, and whether any other substances are being administered. Generally, the amount used will be as recommended by the manufacturer and/or based on empirical studies. In the case of polyamine analogs (or stereoisomer, salt, or protected derivative thereof), the amount will generally be between about 1 to about 300 mg/m$^2$/day, possibly between about 15 to about 150 mg/m$^2$/day. Administration is generally intermittent, meaning that analog (or stereoisomer, salt, or protected derivative thereof) is administered per a period of at least one to two days and then not administered for a period of at least one to two days, with the cycle repeated as indicated. In one embodiment, the polyamine analog (or stereoisomer, salt, or derivative thereof) for 6 days every three weeks.

Routes of administration will generally depend on the nature of the particular polyamine analog (or stercoisomer, salt or protective derivative) used, and may be, for example, oral or by injection (subcutaneous or intravenous). Administration is generally by intravenous or subcutaneous injection.

Preferably, a polyamine analog (or stereoisomer, salt or protected derivative), or other suitable agent that interferes with the polyamine synthetic pathway, polyamine metabolism, and/or the intracellular concentration maintenance of spermine is administered in a suitable pharmaceutical excipient. Pharmaceutical excipients are known in the art and are set forth in Remington: The Science and Practice of Pharmacy, 20th edition, Mack Publishing (2000). The polyamine analog may also be associated with another substance that facilitates agent delivery to macrophages, or increases specificity of the agent to macrophages. For example, an agent(s) may be associated into liposomes. Liposomes are known in the art. The liposomes in turn may be conjugated with targeting substance(s), such as IgGFc receptors. Substances that increase macrophage phagocytosis such as zymosan or tetrachlorodecaoxygen (TCDO) and/or activation such as MCSF, GMCSF or IL-3 may be used to increase uptake of anti-proliferative agent(s).

A polyamine analog (or stereoisomer, salt or protected derivative) may be administered alone, or in conjunction with other substances and/or therapies, depending on the context of administration (i.e., desired end result, condition of the individual, and indications). "In conjunction with" means that an agent is administered prior to, concurrently, or after other substance or therapy. Examples of substances that might be administered in conjunction with an agent include, but are not limited to, riluzole (RILUTEK®). Studies with riluzole, approved by the Food and Drug Administration for therapy of ALS, have demonstrated in statistically significant effects on survival of patients with ALS (Bensimon et al. (1994) *New Eng. J. Med.* 330:585–591; Lacomblez et al. (1996) *Lancet* 347:1425–1431). Often ALS therapy includes treatment aimed at control of symptoms. Accordingly, examples of substances for treatment of symptoms associated with ALS that might be administered in conjunction with an agent include, but are not limited to, baclofen, diazepam, trihexyphenidyl and/or amitriptyline.

The mechanistic effectiveness of various polyamine analogs and enzyme inhibitors can be determined in specific cell lines at least in part by their ability to deplete intracellular polyamine pools. Kramer et al. (1995, *Biochem. Pharmacol.* 50:1433) describe the use of 4-fluoro-L-ornithine to monitor metabolic flux through the polyamine biosynthetic pathway. It was determined that the metabolic flux indicated by the rate of appearance of fluorinated polyamines, reflected the proliferation status of the cells. U.S. Patent No. 5,498,522 outlines the use of SSAT as a prognostic indicator or tumor response marker. Either SSAT enzyme activity, SSAT enzyme protein, or mRNA transcripts can be measured directly, or other determinants related to SSAT induction can be measured, such as SSAT co-factor acetylCoA, and the SSAT products N1-acetylspermine and N1-acetylspermidine. To further determine the effect of a polyamine analog's administration, an individual may be monitored for disease (or precursor disease) progression as well as biochemical and/or genetic markers of disease (or precursor disease). With respect to disease progression, multiple rating scales (i.e., indices of clinical function) have been established and are known in the art for ALS.

Symptoms associated with ALS are known in the art (see, for example, Rowland et al. (2001) *N. Engl. J. Med.* 344: 1688–1700). Such symptoms include, but are not limited to, muscle weakness, decrease in muscle strength and coordination, paralysis, muscle cramps, voice changes and/or hoarseness, speech impairment, difficulty swallowing, gagging or choking easily, difficulty breathing, muscle contractions, muscle atrophy, urinary frequency/urgency, and ankle, feet and leg swelling. ALS symptoms indicated upon neuromuscular examination may include, for example, weakness beginning in one limb or in proximal groups (e.g., shoulders, hips), muscle tremors, spasms, fasciculation, muscle atrophy, clumsy gait and abnormal reflexes.

Other Agents for Modulating Macrophage Proliferation

Besides the polyamine analogs described above, suitable agents for use in modulating macrophages in the context of ALS, include general anti-proliferative agents (i.e., proliferation-modulating agents). These include, but are not limited to, daunomycin, mitomycin C, daunrorubicin, doxorubicin, 5-FU, cytocine arabinoside, colchicine, cytochalasin B, bleomycin, vincristin, vinblastine, methotrexate, cis platinum, ricin, abrin, diphtheria toxin, and saporin.

Other suitable agents would be those which inhibit, or interfere with, the polyamine synthetic pathway, or those which affect the metabolism of polyamines. Other suitable agents are those which affect the closely regulated intracellular concentration of spermidine. An example of such an agent is MGBG (mitoguazone dihydrochloride; XYRKAMINE®; Ilex, Tex.) which inhibits S-adenosylmethionine decarboxylase which in turn is required for the production of polyamines. Any agent that interferes with polyamine interactions with proliferating macrophage target, such as DNA, RNA, and/or membranes would likewise be suitable. Another type of useful agent is one that interferes with polyamine interactions with DNA. Such an agent(s) could exert this function, for example, by any of the effects above (i.e., interfering with the polyamine synthetic pathway and/ or metabolism, disturbing the concentration of intracellular spermine, competitors, etc.) as well as affecting polyamine function in terms of interacting with DNA. It is understood that, with respect to these and any other agent described herein, toxicology considerations also must be taken into account when determining whether, and/or in what amount, an agent is to be used.

It is understood that, with respect to the above-described agents, some can reasonably be considered as, and are considered as, polyamine analogs.

Administration and other considerations have been described above.

The following Examples are provided to illustrate, but not limit, the invention.

EXAMPLES

In general, the flow cytometric methods used in the following examples and appropriate for use in the invention are well known in the art. See, for example, Flow Cytometry: A Practical Approach, 2nd ed., M. G. Ormerod (ed.), Oxford University Press, 1997; Handbook of Flow Cytometry Methods, J. Paul Robinson (ed.), John Wiley & Sons (1993); Current Protocols in Cytometry, J. Paul Robinson (ed.), John Wiley & Sons (October 1997, with periodic updates); Becton Dickinson Cytometry Source Book, Becton Dickinson Immunocytometry Systems (1998, with periodic updates) (San Jose, Calif.).

Example 1

Detection of Abnormal Mononuclear Cells in Peripheral Blood from Patients with ALS Expression of common cell differentiation antigens was examined in peripheral blood mononuclear cells (PBMCs) from amyotrophic lateral sclerosis (ALS) and non-ALS patients. The panel of cell differentiation antigens examined included antigens specific for monitoring changes in monocytes and lymphocytes. Results from the analysis of blood from fifteen ALS patients was compared to results from the analysis of normal, non-ALS family members (3 individuals) and from historical data compiled from patients with lymphoma (11 patients) and from patients with AIDS dementia (2 patients). Participants or their representatives gave informed consent.

The following panel of fluorophore labeled antibodies directed to the indicated antigens were used in the analyses:
fluorescein-conjugated anti-CD8 (Becton Dickinson);
phycoerythrin-conjugated anti-HLA-DR (Becton Dickinson);
phycoerythrin-conjugated anti-CD38 (Becton Dickinson);
peridinin chlorophyll protein-conjugated anti-CD4 (Becton Dickinson);
peridinin chlorophyll protein-conjugated IgG1 (isotype control, Becton Dickinson);
fluorescein-conjugated anti-CD14 (DAKO Corp.);
phycoerythrin-conjugated anti-CD16 (DAKO Corp.);
phycoerythrin-conjugated anti-PCNA (DAKO Corp.);
phycoerythrin-conjugated anti-Ki67 (DAKO Corp.);
fluorescein-conjugated IgG1 (isotype control, DAKO Corp.);
phycoerythrin-conjugated IgG1 (isotype control, DAKO Corp.).

100 µL whole heparinised blood was stained with one or more of the labeled antibodies listed above for 20 minutes at room temperature and protected from light. Red-blood cells were lysed by the addition of 2 ml of FACSLYSE solution (Becton Dickinson, San Jose, Calif.) and a 5 minute incubation. The cell suspensions were centrifuged at 400×g for five minutes. The cell pellets were washed with 1 ml FACSLYSE followed by a wash with 1 ml 0.01 M phosphate-buffered saline (PBS).

For cells not stained for intracelluar antigens, the cells were fixed with 1 ml of 1% paraformaldehyde in 0.01 M PBS, with 0.1% sodium azide.

For cells stained for intracellular antigens, the cells were permeabilized by resuspension in 0.5 ml "Permeabilising Solution" (Becton Dickinson) and incubation at room temperature for 10 minutes. The cells were then washed in 2 ml PBS, centrifuged and resuspended in 0.1 ml PBS. The washed cells were stained with antibodies to intracellular antigens for 30 minutes at room temperature and protected from light. After a wash in 1 ml PBS, the stained cells were fixed with 1 ml of 1% paraformaldehyde in 0.01 M PBS, with 0.1% sodium azide.

Cells were analyzed with a FACSCAN flow cytometer (Becton Dickinson). Antibody staining of the cells was determined by processing at least 10,000 cells per sample through the flow cytometer. Analysis of phenotype was performed by utilizing CELLQUEST software (Becton Dickinson).

The level of expression of major histocompatibility antigen class II (HLA-DR) on the cell surface CD14+ monocytes from ALS patients was compared to the level of expression of HLA-DR on CD14+ monocytes from non-ALS individuals. HLA-DR expression levels on CD14+ cells were quantitated using Becton Dickinson Quantibrite Kit and fluorescence standards. The level of HLA-DR expression was measured as mean/cell fluorescence intensity for the CD14+ population. Statistical analysis using unpaired T-test was used to compare cells from non-ALS individuals to cells from ALS individuals. The results are shown in Table 1.

TABLE 1

Quantitative Expression of HLA-DR in CD 14+ PBMCs

| Non-ALS | HLA-DR (Mean) | ALS | HLA-DR (Mean) |
|---|---|---|---|
| Normal | 525 | GH | 2425 |
| Normal | 979 | AJ | 1327 |
| Normal | 1409 | WC | 887 |
| Lymphoma | 735 | DF | 1011 |
| Lymphoma | 520 | BC | 3140 |
| Lymphoma | 520 | BS | 2863 |
| Lymphoma | 810 | DP | 1871 |
| Lymphoma | 664 | FV | 1371 |
| Lymphoma | 573 | GC | 2146 |
| Lymphoma | 1887 | ML | 1221 |
| Lymphoma | 2192 | FS | 789 |
| AIDS Dementia | 236 | PK | 1662 |
| AIDS Dementia | 1263 | GD | 813 |
| Lymphoma (post-trans) | 823 | DK | 1235 |
| Lymphoma (post-trans) | 822 | SR | 1181 |
| Lymphoma (post-trans) | 1585 | | |
| Mean | 973 | | 1596 (P ≦ 0.01) |

As shown in Table 1, the results indicate that CD14+ monocytes from ALS patients expressed significantly higher levels of HLA-DR on their cell surface as compared to CD14+ monocytes from non-ALS individuals. The expression of surface HLA-DR on quantitation showed a 64% increase in surface HLA-DR levels and was statistically significant (P≦0.01).

Generally, monocytes express high level of HLA-DR on activation and differentiation into tissue macrophages and non-stimulated circulating monocytes express low levels of HLA-DR. Thus, the data presented herein show that circulating monocytes in ALS patients are generally activated and that they are differentiating into macrophages.

Heparinized blood was assayed for cell marker expression as described above one day after the blood was collected ("second day" cells). Monocytes from these ALS patients and from non-ALS individuals were analyzed for evidence of proliferation using proliferation markers proliferating cell nuclear antigen (PCNA) and Ki67 reactivity. PBMCs were stained with anti-CD14 and with anti-PCNA or anti-Ki67 and analyzed as described above. The results are shown in Table 2.

TABLE 2

Expression of antigens in CD14+ PBMCs

| Marker or Antigen | ALS | non-ALS |
|---|---|---|
| side scatter | 386 | 361 |
| % CD14/HLA-DR | 93 | 93 |
| % CD14/CD16 | 29 | 23 |
| % CD14/PCNA | 35 | 32 |
| % CD14/Ki67 | 2.48 | 0.4 |

As shown in Table 2, PCNA reactivity was within the normal range in ALS patients. However, Ki67 positive CD14+ cells appear to be elevated in ALS patients. Ki67 and PCNA are expressed at various stages of cell cycle. Thus, the Ki67 reactivity of the CD14+ cells of ALS patients indicates that the cells were mitotic.

The PBMCs were also analyzed for T lymphocyte markers and the results are shown in Table 3.

TABLE 3

Expression of lymphocytic antigens in CD14+ PBMCs

| Antigen | ALS | non-ALS |
|---|---|---|
| % CD4 | 45 | 41 (28–52) |
| % CD8 | 21 | 29 (16–45) |
| CD4/CD8 | 2.57 (1.2–6.1)* | 1.37 (0.7–3.0) |
| % CD4/CD38 | 24 | 19 |
| Median CD4/CD38 | 11 | 4 |
| % CD8/CD38 | 11 | 9 |
| Median CD8/CD38 | 2 | 1 |

*$P \leq 0.01$

As shown in Table 3, analysis of the PBMCs with T lymphocyte markers did not show any evidence of T lymphocyte activation. CD4 and CD8 levels were within normal ranges. The activation status of lymphocytes as measured by CD4/CD38 and CD8/CD38 reactivity ratios were also within normal ranges, suggesting that this component of the immune system is generally normal.

Figure 2:
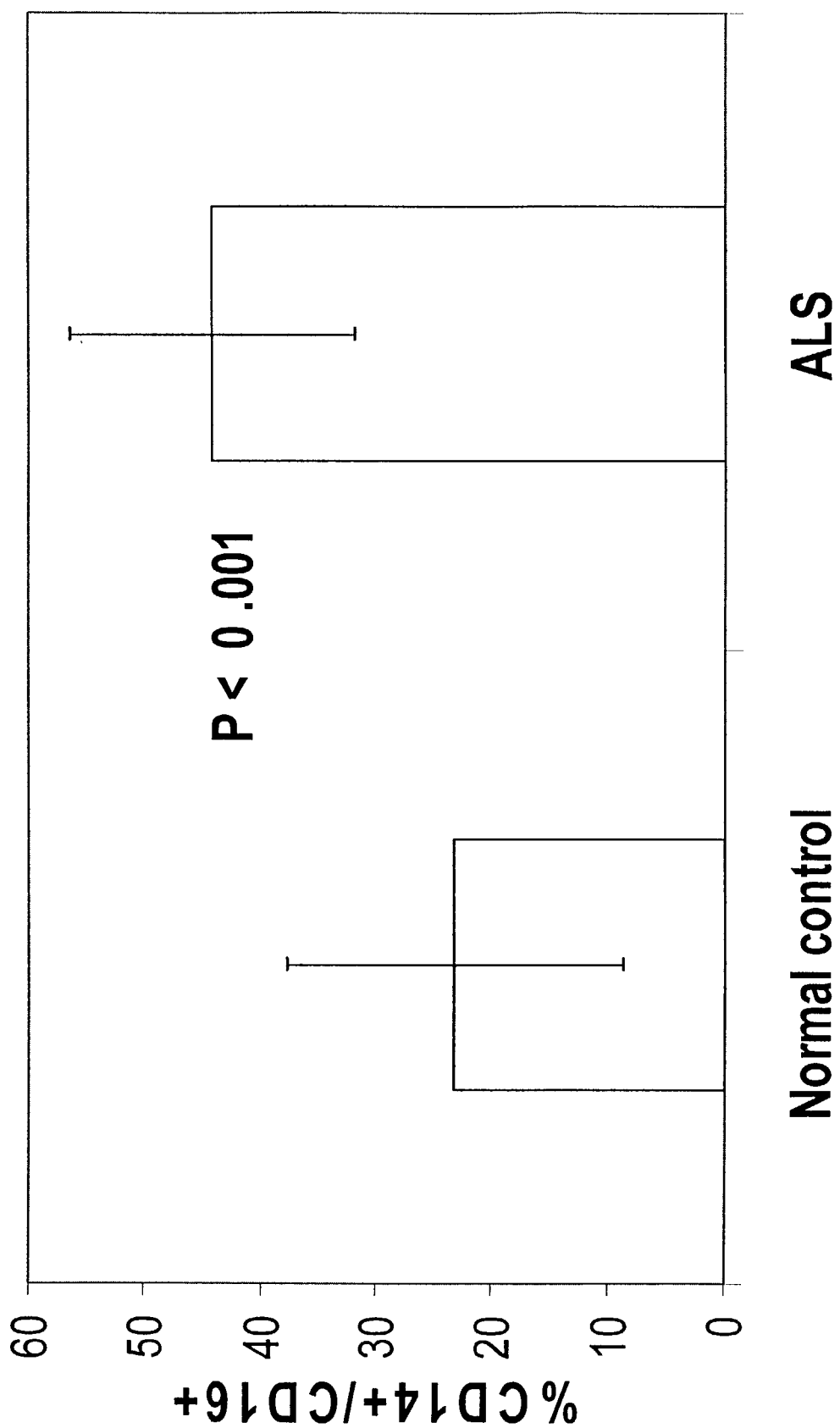
FIG. 2 is a bar graph depicting the percentage of CD16+ cells in the population of CD14+ cells from peripheral blood samples of ALS patients (ALS) and non-ALS individuals (normal control).

In a another experiment, results from the analysis of blood from twenty ALS patients was compared to results from the analysis of blood from twenty normal, non-ALS individuals. Whole heparinised blood was analyzed for cell marker expression as described above on the same day as the blood was collected ("same day" cells). FIG. 1 depicts the results of the level of expression of HLA-DR on CD14+ monocytes from the same day blood samples. FIG. 2 depicts the percentage of CD14+ cells co-expressing CD16 in the same day blood samples.

As shown in FIG. 1, CD14+ monocytes from ALS patients expressed significantly higher levels of HLA-DR on their cell surface as compared to CD14+ monocytes from non-ALS individuals. FIG. 2 shows that the percentage of CD16+ cells in the population of CD14+ cells is significantly elevated in the blood of ALS patients compared to that in the blood of non-ALS individuals.

In sum, CD14+ cells from PBMCs of ALS patients show alterations in surface markers that suggest abnormality in cell activation, differentiation and proliferation. For example, the monocytic compartment shows evidence of activation, although no major changes in activation status of lymphocytes were observed.

Example 2

Effect of Blood Collection Conditions on the Identification of Abnormal Circulating Macrophages from ALS Patients Cell marker expression analysis was performed, as described above, on seven blood samples from ALS patients drawn into heparin-containing tubes and on blood samples drawn into tubes containing the calcium chelator acid citrate dextrose ("ACD" tubes). Ten blood samples from normal, non-ALS individuals drawn into heparin-containing tubes were also analyzed for cell marker expression as described above on the same day that the blood was collected.

Figure 3:
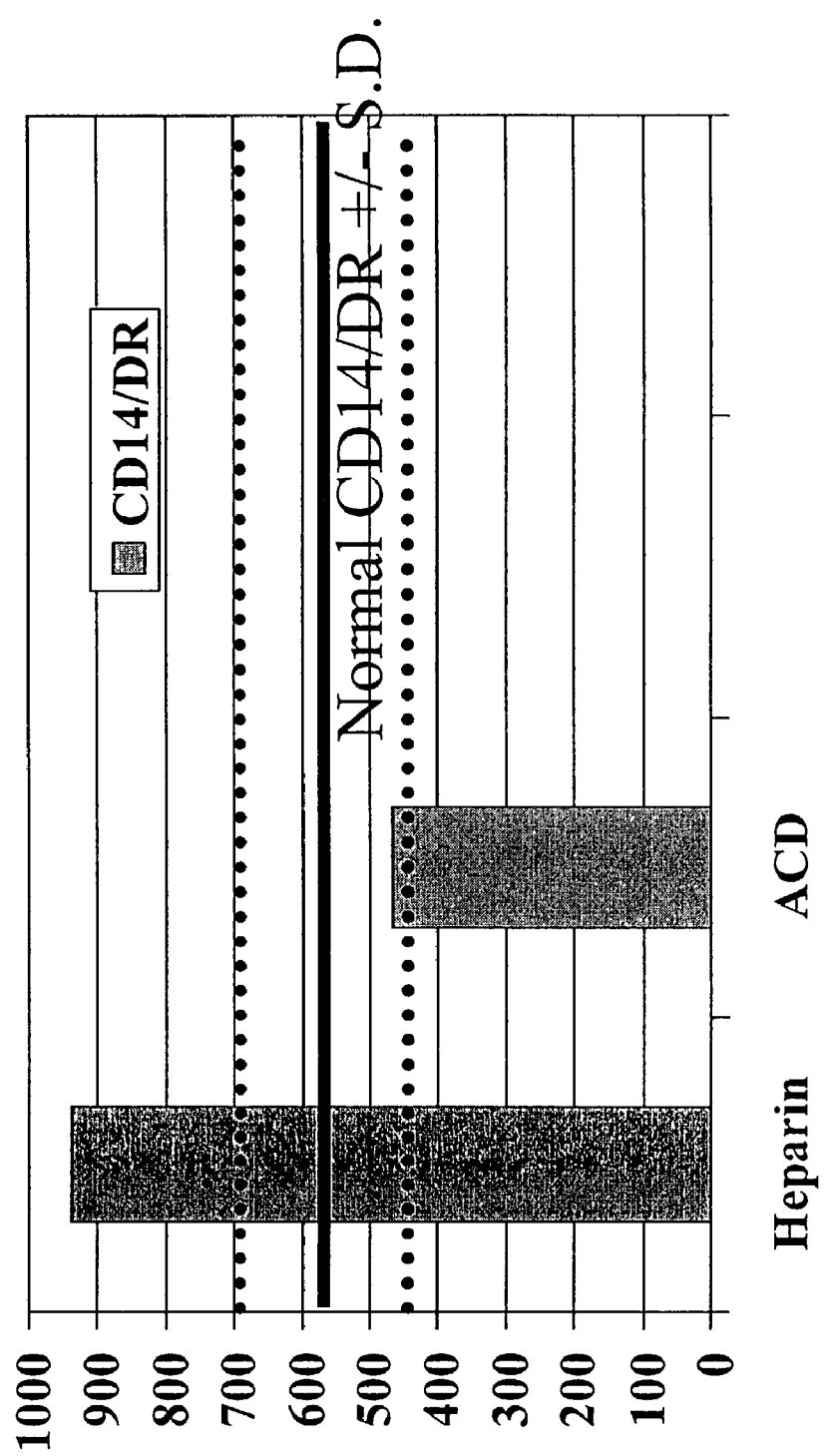
FIG. 3 is a bar graph depicting the level of HLA-DR expression on CD14+ monocytes from peripheral blood samples of ALS patients when the blood was collected in heparin tubes versus when the blood was collected in tubes with the calcium chelator ACD. The HLA-DR expression values of CD14+ cells of non-ALS individuals (normal) from peripheral blood samples collected in heparin tubes are depicted as the solid horizontal line for the median and as the dotted lines above and below the median for the standard deviation.
Figure 4:
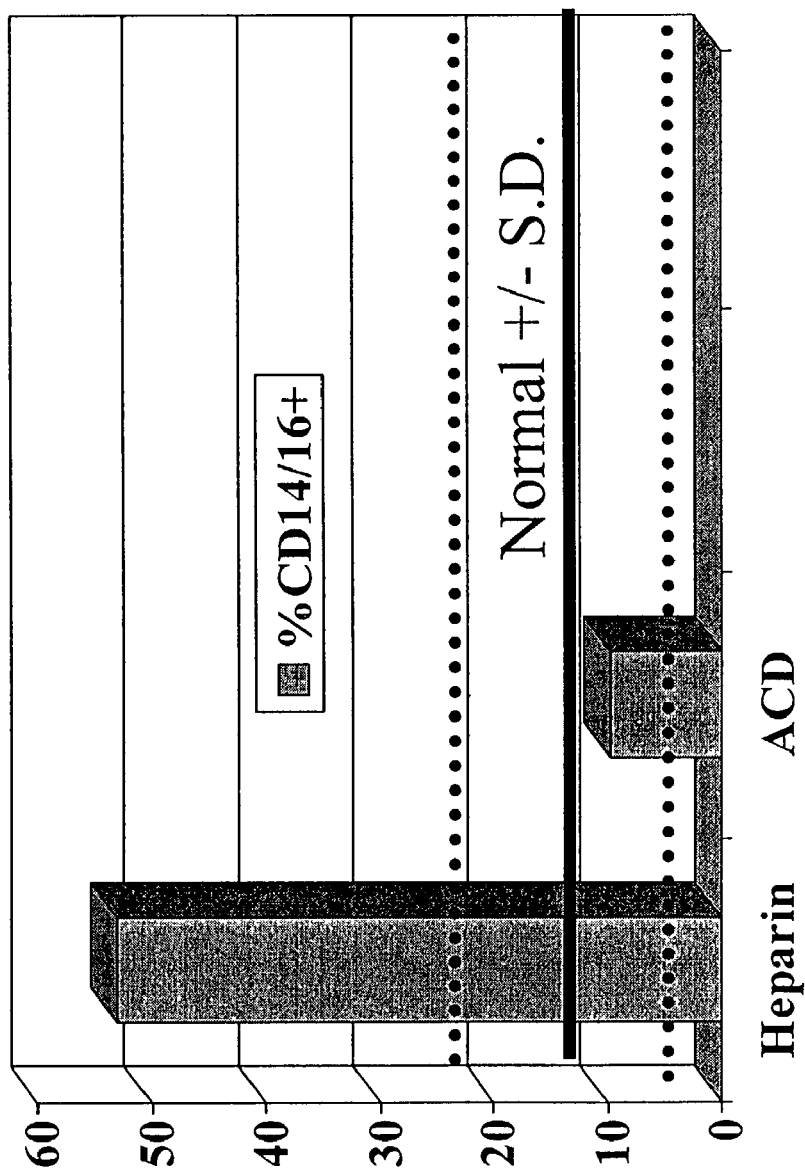
FIG. 4 is a bar graph depicting the percentage of CD16+ cells in the population of CD14+ cells from peripheral blood samples of, ALS patients when the blood was collected in heparin tubes versus when the blood was collected in tubes with the calcium chelator ACD. The percentage of CD14+/CD16+ cells of non-ALS individuals (normal) from peripheral blood samples collected in heparin tubes are depicted as the solid horizontal line for the median and as the dotted lines above and below the median for the standard deviation.

FIG. 3 depicts the level of expression of HLA-DR on CD14+ monocytes from the ALS blood samples collected in heparin tubes versus the ALS blood samples collected in ACD tubes. FIG. 4 depicts the percentage of CD14+ cells co-expressing CD16 in the ALS blood samples collected in heparin tubes versus the ALS blood samples collected in ACD tubes. In FIGS. 3 and 4, the values from the normal samples collected in heparin are depicted as the solid horizontal line for the median and the dotted lines above and below the median for the standard deviation.

As shown in FIGS. 3 and 4, with chelation of calcium in the collected blood sample, the level of both the level of HLA-DR expression on CD14+ cells and the percentage of CD16+/CD14+ cells fall to normal levels in the same day analyzed ALS blood. Similar results were obtained when EDTA was used as the calcium chelator. This indicates that calcium chelation in cell medium leads to a loss of the abnormal macrophages characteristic of ALS. This also suggests that sufficient unchelated calcium in the cell medium is necessary for the detection of the two significant macrophage activation parameters that differentiate the ALS samples from control samples.

Example 3

Effect of Polyamine Analogs on CD14+ Monocytes from Patients with ALS

Peripheral blood mononuclear cells (PBMCs) are isolated from heparin-treated whole blood by layering over Percoll, density 1.087, (Pharmacia, Piscataway, N.J.) and followed by centrifugation at 800×g. The cells that collect at the Percoll/plasma interface are harvested and washed with 0.01 M phosphate-buffered saline (PBS). Isolated cells are then suspended in RPMI 1640 culture medium, with 10% fetal bovine serum, at a concentration of about $1 \times 10^6$ cells/ml. Cells are allocated to polyvinyl culture tubes at 1 ml/tube. A polyamine analog such as SL-11047 is added to 3 tubes, to achieve final concentrations of 1.0, 0.1, and 0.01 micromolar. A fourth tube, for control, receives no (zero) drug. All tubes are then placed in a humidified incubator, at 37 degree centigrade, 5% carbon dioxide, for five days.

On the 5$^{th}$ day of incubation, cells are removed from the incubator, washed with PBS and resuspended in PBS at 0.1 ml/tube. Detection of monocytes is detected by addition of fluorescein-conjugated anti-CD14 (DAKO Corp., Carpenteria, Calif.), for 20 minutes, at room temperature, protected from light. A parallel aliquot is stained with control fluorescein-conjugated IgG1 (isotype antibody control, DAKO Corp.) to serve as a negative stain control. The cells are washed with PBS and fixed by addition of 1 ml of 1% paraformaldehyde in PBS, with 0.1% sodium azide. CD14+ monocytes are identified by processing 20,000 cells/tube through a FACSCAN Flow Cytometer (Becton Dickinson, San Jose, Calif.), driven by CELLQUEST software (Becton Dickinson). The numbers of CD14+ monocytes in drug-treated samples are compared to non-treated controls, and the drug dose required to achieve 50% depletion calculated (ED 50).

Figure 5:
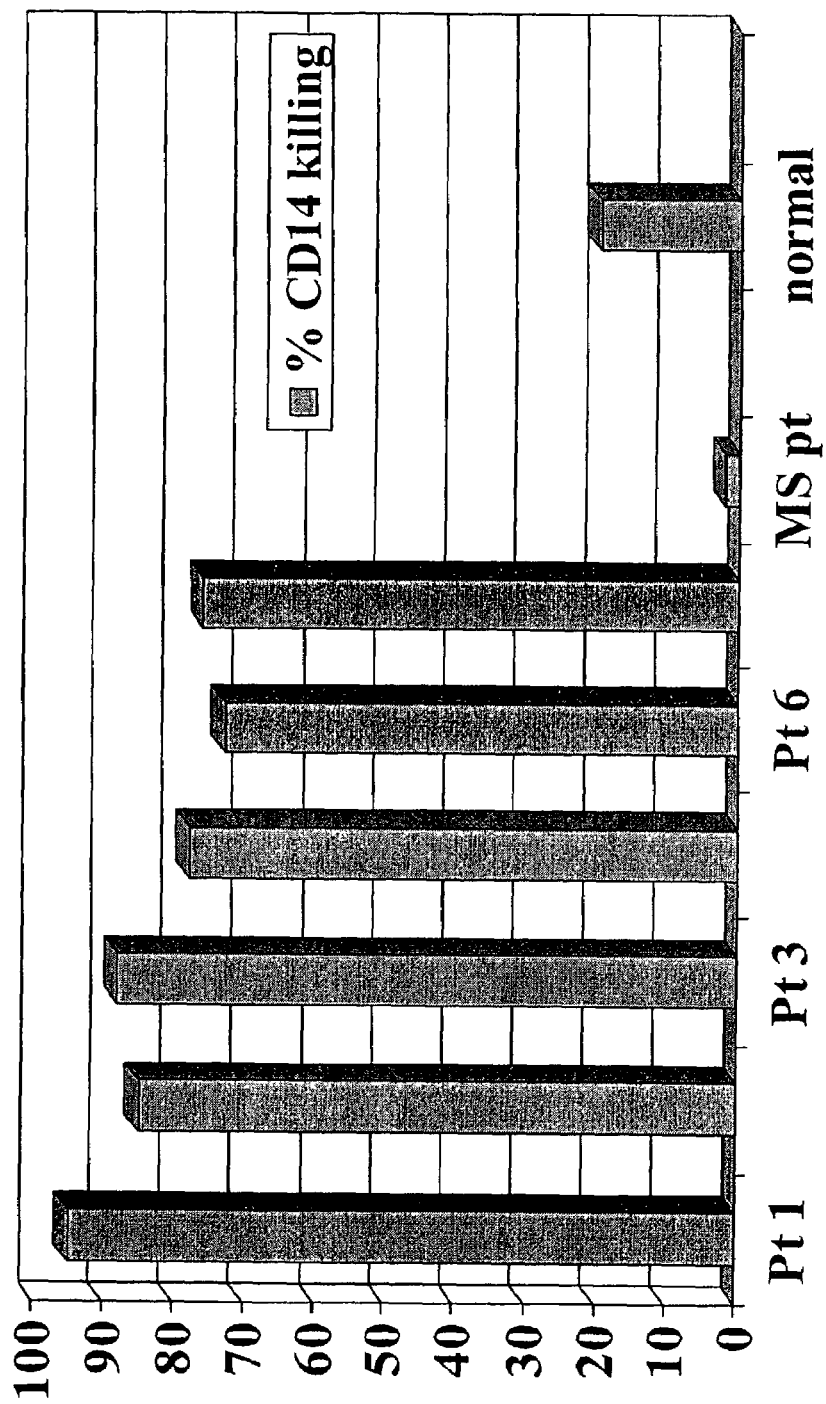
FIG. 5 is a bar graph depicting percent killing of CD14+ cells from peripheral blood samples after treatment with 1 μM of a polyamine analog. The samples depicted were from six ALS patients (Pt 1–Pt 6), one multiple sclerosis patient (MS pt); one normal individual.

An experiment as described above was performed with CD14+ circulating monocytes from 6 ALS patients, 1 multiple sclerosis (MS) patient and 1 normal (non-ALS) control subject. In this experiment, the cells from a patient were incubated with or without polyamine analog SL-11047 for 6 days and survival of CD14+ cells was determined. FIG. 5 depicts the results of the percentage of cells killed in the presence of 1.0 µM SL-11047 for the various cell samples. This experiment demonstrates that CD14+ circulating monocytes from ALS patients are substantially more susceptible to killing by polyamine analogs than CD14+ circulating monocytes of a normal subject or an MS patient. This differential in susceptibility to killing is presumably due to the polyamine analog killing effect on the abnormal macrophage population of circulating CD14+ monocytes in the ALS patients. Thus, polyamine analogs are likely useful in decreasing the level of abnormal macrophages in ALS patients.

What is claimed is:

1. A method of screening for an agent effective in decreasing the number of abnormal macrophages associated with ALS, comprising
    determining the difference in viability of $CD14^+$ cells with elevated HLA-DR expression or $CD14^+/CD16^+$ cells in the presence and in the absence of a candidate agent,
    wherein the $CD14^+$ cells with elevated HLA-DR expression or the $CD14^+/CD16^+$ cells are obtained from a blood sample from an individual with ALS, and
    wherein a decrease in viability of $CD14^+$ cells with elevated HLA-DR expression or $CD14^+/CD16^+$ cells caused by the candidate agent indicates that the candidate agent is effective in decreasing the number of abnormal macrophages associated with ALS.

2. The method according to claim 1, wherein the viability of $CD14^+$ cells with elevated HLA-DR expression is determined.

3. The method according to claim 1, wherein the viability of $CD14^+/CD16^+$ cells is determined.

* * * * *